(12) United States Patent
Gupta

(10) Patent No.: US 12,305,183 B2
(45) Date of Patent: May 20, 2025

(54) COMPOSITIONS AND METHODS FOR PROTECTING HOSTS AGAINST PATHOGEN INFECTIONS

(71) Applicant: Innate Immunity LLC, Santa Fe, NM (US)

(72) Inventor: Goutam Gupta, Santa Fe, NM (US)

(73) Assignee: Innate Immunity LLC, Santa Fe, NM (US)

( * ) Notice: Subject to any disclaimer, the term of this patent is extended or adjusted under 35 U.S.C. 154(b) by 217 days.

(21) Appl. No.: 16/479,860

(22) PCT Filed: Jan. 23, 2018

(86) PCT No.: PCT/US2018/014905
§ 371 (c)(1),
(2) Date: Jul. 22, 2019

(87) PCT Pub. No.: WO2018/136962
PCT Pub. Date: Jul. 26, 2018

(65) Prior Publication Data
US 2021/0054034 A1 Feb. 25, 2021

Related U.S. Application Data

(63) Continuation of application No. 15/412,420, filed on Jan. 23, 2017, now abandoned.

(51) Int. Cl.
*C12N 15/82* (2006.01)
*A01N 37/46* (2006.01)
*C07K 14/415* (2006.01)
*C12N 9/50* (2006.01)

(52) U.S. Cl.
CPC ......... *C12N 15/8281* (2013.01); *A01N 37/46* (2013.01); *C07K 14/415* (2013.01); *C12N 9/63* (2013.01); *C12N 15/8241* (2013.01); *C12Y 304/21064* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford et al. | |
| 5,262,316 A | 11/1993 | Engler et al. | |
| 5,268,526 A | 12/1993 | Hershey et al. | |
| 5,569,831 A | 10/1996 | Dellapenna | |
| 5,589,615 A | 12/1996 | De Clercq et al. | |
| 5,597,945 A | 1/1997 | Jaynes et al. | |
| 5,679,558 A | 10/1997 | Gobel et al. | |
| 5,750,871 A | 5/1998 | Moloney et al. | |
| 8,592,652 B2 | 11/2013 | Frank et al. | |
| 2004/0031072 A1 | 2/2004 | La Rosa et al. | |
| 2005/0257285 A1* | 11/2005 | Gupta | C07K 14/43563 |
| | | | 435/468 |
| 2009/0158470 A1* | 6/2009 | Gupta | C07K 14/4723 |
| | | | 800/301 |
| 2016/0312241 A1 | 10/2016 | Stover et al. | |

FOREIGN PATENT DOCUMENTS

| | | |
|---|---|---|
| WO | WO-2010/149792 A2 | 12/2010 |
| WO | WO-2014/145964 A1 | 9/2014 |
| WO | WO-2018/136962 A1 | 7/2018 |

OTHER PUBLICATIONS

Locus XP_010653029. NCBI. "Predicted: defensin-like protein 1 isoform X2 [Vitis vinifera]". (Year: 2016).*
Locus XP_002272020. NCBI. "Predicted: putative BPI/LBP family protein At1g04970 [Vitis vinifera]". (Year: 2016).*
Genbank accession XP_002272020.1 (Year: 2016).*
Genbank accession XP_002274353.1 (Year: 2016).*
Genbank accession CAN83425.1 (Year: 2008).*
Beamer, Lesa J., et al., "The BPI/LBP family of proteins: A structural analysis of conserved regions", Protein Science, 1998, pp. 906-914, vol. 7, 1998 The Protein Society.
Belaaouaj, Abderr Azzaq, et al., "Degradation of Outer Membrane Protein A in *Escherichia coli* Killing by Neutrophil Elastase", Science, 2000, pp. 1185-1187, vol. 289.
Cao, Jun et al., "Genome-wide and molecular evolution analysis of the subtilase gene family in *Vitis vinifera*", BMC Genomics, 2014, pp. 1-15, vol. 15, No. 1116.
Dandekar et al., "Building a next generation chimeric antimicrobial protein to provide rootstock-mediated resistance to Pierces disease in grapevines", Pierce's disease control program: Symposium Proceedings Dec. 15-17, 2014, pp. 99-105.
Dandekar et al., "Building a next generation chimeric antimicrobial protein to provide rootstock-mediated resistance to Pierces disease in grapevines", Pierce's disease research progress reports, Dec. 2012, pp. 89-93.
Dandekar et al., "Field testing transgenic grapevine rootstocks expressing chimeric antimicrobial protein and polygalacturonase-inhibiting protein", Pierce's disease and other designated pests and diseases of winegrapes, Dec. 1, 2017, pp. 20-28.
Dandekar, Abhaya M., et al., "An engineered innate immune defense protects grapevines from Pierce disease", PNAS, Mar. 6, 2012, pp. 3721-3725, vol. 19, No. 10.
Giacomelli, Lisa, et al., "Identification and Characterization of the Defensin-Like Gene Family of Grapevine Lisa", MPMI, 2012, pp. 1118-1131, vol. 25, No. 8.
Iizasa, Sayaka, et al., "*Arabidopsis* LBP/BPI relaled-1 and -2 bind to LPS directly and regulate PR1 expression", Scientific Reports, 2016, pp. 1-10, vol. 6, No. 27527.

(Continued)

*Primary Examiner* — Matthew R Keogh
*Assistant Examiner* — David R Byrnes
(74) *Attorney, Agent, or Firm* — Foley & Lardner LLP

(57) ABSTRACT

A chimeric protein and method of creating genetically altered plant and parts thereof with a chimeric protein wherein the chimeric protein comprises a recognition element and a lysis element connected by a linker wherein the recognition element binds to a pathogen and the lysis element lyses the pathogen and wherein the recognition element is derived from a first protein and the lysis element is derived from a second protein wherein the first protein and the second protein are endogenous to the host to be treated with the chimeric protein.

13 Claims, 5 Drawing Sheets

Specification includes a Sequence Listing.

(56) References Cited

OTHER PUBLICATIONS

International Search Report and Written Opinion of the International Searching Authority issued in International Application No. PCT/US2018/014905, dated May 4, 2018.
Meyer, Michael, et al., "The subtilisin-like protease SBT3 contributes to insect resistance in tomato", The Journal of Experimental Botany, 2016, pp. 4325-4338, vol. 67, No. 14.
Pelegrini, Patricia B., et al., "Plant gamma-thionins: Novel insights on the mechanism of action of a multi-functional class of defense proteins", The International Journal of Biochemistry & Cell Biology, 2005, pp. 2239-2253, vol. 37, No. 11, Elsevier Ltd.
Raj, Periathamby Antony, et al., "Current status of defensins and their role in innate and adaptive immunity", FEMS Microbiology Letters, 2002, pp. 9-18, vol. 206, Elsevier Science B.V.
Romero, Alicia, et al., "Processing of thionin precursors in barley leaves by a vacuolar proteinase", Eur. J. Biochem., 1997, pp. 202-208, vol. 243.
Silva, Christopher J., et al., "Proteinase K and the structure of PrP$^{Sc}$: The good, the bad and the ugly", Virus Research, 2015, pp. 120-126, vol. 207.
Szankowski, I., "Transformation of apple (*Malus domestica* Borkh.) with the stilbene synthase gene from grapevine (*Vitis vinifera* L.) and a PGIP gene from kiwi (*Actinidia deliciosa*)", Plant Cell Rep., 2003, pp. 141-149, vol. 22, Springer-Verlag 2003.
Tornero, Pablo, et al., "Identification of a New Pathogen-induced Member of the Subtilisin-like Processing Protease Family from Plants", The Journal of Biological Chemistry, 1997, pp. 14412-14419, vol. 272, No. 22, The American Society for Biochemistry and Molecular Biology, Inc.
"*Arabidopsis* LBP/BPI related-1 and -2 bind to LPS directly and regulate PR1 expression", Sayaka Iizasa?, Scientific Reports, Article No. 27527.
"Predicted: Vitis vinifera defensin-like protein1(LOC100252765), transcript variant X2, mRNA", Genbank, Accession No. XM_010654727.2.
"Predicted: Vitis vinifera subtilisin-like protease SBT6.1 (LOC100264570),mRNA", Genbank, Accession No. XM_002280906.3.
"Predicted: putative BPI/LBP family protein Atlg04970 [Vitisvinifera]", Genbank, Accession No. XP_002272020.1.
Dong, Yan et al. Application and prospect of antimicrobial peptides in biological engineering of Chinese materia medica. Chinese Traditional and Herbal Drugs. p. 780-783.
Mao, Dandan et al. Comparison of extraction methods of activated sludge microbial DNA for PCR-DGGE analysis. Chinese Journal of Environmental Engineering. p. 1189-1195.

\* cited by examiner

FIG. 1

Recognition Targets on Xf
- Lipopolysaccharide
- mopB

Outer membrane

Periplasmic space and Peptidoglycan

Inner membrane

FIG. 4

• BPI/LBP_Thionin

```
  1 mrpsvlvifi afilfitpsqa hlkstessfi silissqgld fiknllitka lssltplqlp
 61 gikksvkipf lgrvdiafsn itiyhidvss sniapgdtgv aliasgttcn lsmnwhysyn
121 twfvpveisd sgtaqvqveg mevgltlgle nregsmklsa kdcgcyvedi sikldggasw
181 lyggvvdafe eqigsavest itkklkegil kldsflqalp keipvdnias lnvtfvndpl
241 lsnssigfdi ngfftranat tlpkyyqnsr hpvsctdpsk rvcesqshkf egacmgdhnc
301 alvcrneqfs qqkckglrrr cfctklc
```

• Thionin_BPI/LBP

```
  1 merkslqfff flllillasq mvvpsearvc esqshkfeqa cmgdhncalv crneqfsqqk
 61 ckglrrrcfc tklcgstapp assqgldftik nllitkaiss ltplqlpqik ksvkipflgr
121 vdiafsniti yhidvsssni apgdtgvaii asgttcnlsm nwhysyntwf vpveisdsgt
181 aqvqvegmev gltlglenre gsmklsakdc gcyvedisik ldggaswlyg gvvdafeeqi
241 gsavestitk klkegilkid sflqalpkei pvdniaslnv tfvndpllsn ssigfdingl
301 ft
```

• Thionin_Proteinake K

```
  1 merkslqfff flllillasq mvvpsearvc esqshkfeqa cmgdhncalv crneqfsqqk
 61 ckglrrrcfc tklcgstapp arqlwekqvt qakvkmaifd tqiranhphf rnikertwwt
121 nedtlndnlq hqtfvagvia gqvdeclqfa pdtelyafrv ftdaqvsvts wfldafnyai
181 atnmdvlnls iggpdyldip fvekvwelta nniimvsaiq ndqplygtln npadgsdvig
241 vidyqdhias fssrqmstwe iphqvqrvkp dvvaygreim qssisancks lsqtsvaspv
301 vaqvvcllvs vipehdrkni lnpasmkgal veqaarlpda nmveqgaqr
```

• Proteinase K_Thionin

```
  1 mtlqrrlaci flacvvipall iggtalaser glwekqvtga kvkmaifdtg iranhphfrn
 61 ikertnwtne dtlndnlghg tfvagviagg ydeclgfapd telyafrvft daqvsytswf
121 ldafnyaiat nmdvlnlsig gpdyldlpfv ekvweltann iimvsaignd gplygtlnnp
181 adqsdvigvi dyqdhiasfs sqrgmstweip pehdrknlin pasmkqalve vayqreimqs sisancksls
241 gtsvaspvva gvvcllvsvi pehdrknlin pasmkqalve gaarlpdanm yeggagrgst
301 apparvcesg shkfeegacmg dhncalvcrn egfsgqkckg lrrrcfctkl c
```

Italics: BPI/LBP or proteinase K
Bold: Linker
Italics Underline Bold: Thionin
Underline: Signal sequence

COMPOSITIONS AND METHODS FOR PROTECTING HOSTS AGAINST PATHOGEN INFECTIONS

RELATED APPLICATIONS

The present application claims priority under 35 U.S.C. § 371 to International Patent Application No. PCT/US2018/014905, filed Jan. 23, 2018, which claims priority to and the benefit of U.S. patent application Ser. No. 15/412,420, filed Jan. 23, 2017. The contents of these applications are hereby incorporated by reference in their entireties.

STATEMENT REGARDING FEDERALLY SPONSORED RESEARCH OR DEVELOPMENT

Not Applicable.

SEQUENCE LISTING SUBMITTED VIA EFS-WEB

The instant application contains a Sequence Listing which has been submitted electronically in ASCII format and is hereby incorporated by reference in its entirety. The content of the ASCII text file of the sequence listing, created on Jan. 16, 2017, is named Anti_Xf_Chimera_011618_ST25.txt and is 53 Kbytes in size and is electronically submitted via EFS-Web.

INCORPORATION BY REFERENCE OF MATERIAL SUBMITTED ON A COMPACT DISC

Not Applicable.

BACKGROUND OF THE INVENTION

Antibiotics are commonly used to target specific genes of both gram-positive and gram-negative bacteria and clear them before they can cause physiological damage to an infected host. However, over the last two decades, the widespread use of rapid emergence of antibiotic resistance involving mutations in target genes, efficient efflux of antibiotics, horizontal transfer of resistance genes, etc., severely limited their clinical use (Peschel, 2002, Trends Microbiol. 10:179). The clinical world witnessed an alarming trend in which several gram-positive and gram-negative have become increasingly resistant to commonly used antibiotics, such as penicillin and vancomycin.

The discovery of linear anti-microbial proteins, such as the insect cecropins, and disulfide-bridged anti-microbial proteins, such as the defensins, initially raised hopes that antimicrobial proteins (AMPs) can become a viable alternative to antibiotics. Both cecropins and defensins have been evolutionarily conserved in invertebrates and vertebrates and constitute the first line of host innate immune defense (Boman, 2003, J. Int. Med. 254: 197-215; Raj & Dentino, FEMS Microbiol. Lett., 202, 9, 2002; Hancock The LANCET 1, 156, 201). Members of the cecropin and defensin/thionin families have been isolated from plants, insects, mammals, and humans. They are normally stored in the cytoplasmic granules of plant, insect, and human cells and undergo release at the site of pathogen attack. Rather than targeting intracellular bacterial machinery, positively charged AMPs interact with the negatively charged (and somewhat conserved) membrane components, i.e., membrane peptidoglycan (PGN) in gram-positive bacteria and lippopolysaccharide (LPS) in gram-negative bacteria. In addition, AMPs target also viral and fungal membranes (world wide webncbi.nlm.nih.gov/pmc/articles/PMC1497874/).

Following the identification and initial characterization of the cecropins and defensins/thionins, it was anticipated that these peptides would not be subject to microbial resistance. Defensins/thionins are antimicrobial peptides that act mainly by disrupting the structure of bacterial cell membranes. However, it was soon discovered that both gram-positive and gram-negative bacteria can develop resistance against these anti-microbial proteins by modifying their membrane glycolipid components. These modifications probably weaken the initial interaction of these anti-microbial peptides with the membrane glycolipid and thereby significantly reduce their ability to form pores and lyse bacterial membrane.

Globally, one-fifth of potential crop yield is lost due to plant diseases, primarily as a result of bacterial pathogens. For example, *Xylella fastidiosa* (Xf) is a devastating bacterial pathogen that causes Pierce's Disease in grapevines (Davis et al., 1978, Science 199: 75-77), citrus variegated chlorosis (Chang et al., 1993, Curr. Microbiol. 27: 137-142), alfalfa dwarf disease (Goheen et al., 1973, Phytopathology 63: 341-345), and leaf scorch disease or dwarf syndromes in numerous other agriculturally significant plants, including almonds, coffee, and peach (Hopkins, 1989, Annu. Rev. Phytopathol. 27: 271-290; Wells et al., 1983, Phytopathology 73: 859-862; De Lima, et al., 1996, Fitopatologia Brasileira 21(3)). Many agriculturally important plants are susceptible to diseases caused by Xf. In the majority of plants Xf behaves as a harmless endophyte (Purcell and Saunders, 1999, Plant Dis. 83: 825-830). Different Xf strains infect different plant hosts (Hendson, et al., 2001, Appl. Environ. Microbiol 67: 895-903). For example, certain strains cause disease in specific plants, while not in others. Additionally, some strains will colonize a host plant without causing the disease that a different Xf strain causes in the same plant. Similar situations are encountered in *Xanthamonas* and *Pseudomonas* strains (jb.asm.org/content/82/6/913.full.pdf)

Xf is acquired and transmitted to plants by leafhoppers of the Cicadellidae family and spittlebugs of the Cercropidae family (Purcell and Hopkins, 1996, Annu. Rev. Phytopathol. 34: 131-151). Once acquired by these insect vectors, Xf colonies form a biofilm of poorly attached Xf cells inside the insect foregut (Briansky et al., 1983, Phytopathology 73: 530-535; Purcell et al., 1979, Science 206: 839-841). Thereafter, the insect vector remains a host for Xf propagation and a source of transmission to plants (Hill and Purcell, 1997, Phytopathology 87: 1197-1201). In susceptible plants, Xf multiplies and spreads from the inoculation site into the xylem, where it forms colonies that eventually occlude xylem vessels, blocking water transport.

Pierce's disease is an Xf-caused lethal disease of grapevines in North America through Central America, and has been reported in parts of northwestern South America. It is present in some California vineyards annually, and causes the most severe crop losses in Napa Valley and parts of the Central Valley. Pierce's Disease is efficiently transmitted by the glassy-winged sharpshooter insect vector. In California, the glassy-winged sharpshooter is expected to spread north into the citrus belt of the Central Valley and probably will become a permanent part of various habitats throughout northern California. It feeds and reproduces on a wide variety of trees, woody ornamentals and annuals in its region of origin, the southeastern United States. Crepe myrtle and sumac are especially preferred. It reproduces on *Eucalyptus* and coast live oaks in southern California.

Over the years, a great deal of effort has been focused on using insecticides to eliminate the spread of pathogens including Xf. However, insecticides have not eliminated the causative Xf. For example, there remains no effective treatment for Pierce's Disease. Other crops found in these regions of the State of California have also been effected, including the almond and oleander crops. The California Farm Bureau reports that there were 13 California counties infested with the glassy-winged sharpshooter in the year 2000, and that the threat to the State of California is $14 billion in crops, jobs, residential plants and trees, native plants, trees and habitats.

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

BRIEF SUMMARY OF THE INVENTION

One embodiment of the present invention provides a compound for use in treating a host, the compound comprising a recognition element and a lysis element connected by a linker wherein the recognition element binds to a surface protein on the pathogen and the lysis element lyses the pathogen and wherein the recognition element is derived from a first protein and the lysis element is derived from a second protein wherein the first protein and the second protein are endogenous to the host (for example a plant, animal or human). For example, the compound is a chimeric protein for treating a host infected or at risk of becoming infected with a pathogen that causes disease in the host. Further, the recognition element comprises either a sequence derived from subtilisin such as a Proteinase K amino acid sequence or portion thereof, or a sequence with homology thereto, or a bactericidal permeability-increasing protein (BPI)/Lipopolysaccharide-binding protein (LBP) protein amino acid sequence, or portion thereof or a sequence with homology thereto. For example, the recognition element has a specific binding affinity to an outer-membrane protein such as mopB on the surface of the pathogen. Further still, the lysis element comprises a definsin sequence such as a thionin amino acid sequence, or a portion thereof or a sequence with homology thereto.

In one embodiment, the lysis element is selected from the group consisting of SEQ ID NOs: 2, 9, 10, 15, and 35 or a sequence with homology thereto and the recognition element is selected from the group consisting of SEQ ID NOs 1, 3, 5, 8, 11, 12, 16, 34, and 36 or a sequence with homology thereto. Further still, the linker is an amino acid sequence ranging in length, for example, from 1-50 amino acids in length. For example, the linker may be selected from the group consisting of Arginine-Tryptophan, Serine-Arginine-Aspartic Acid, SEQ ID NO 17-23 and 26-28, and amino acid sequences having homology thereto. In another embodiment, the chimeric protein has an amino acid sequence selected from the group consisting of SEQ ID NO: 4, 5, 6, 7, 30, 31, 32, and 33 or an amino acid sequence with homology thereto. In one embodiment the chimeric protein is encoded for by a polynucleotide comprising a nucleic acid sequence. For example, the polynucleotide is operably linked to a promoter to produce an expression vector. The amino acid sequence homology is 50% or greater, 60% or greater, 70% or greater, 80% or greater, 90% or greater, 95% or greater. In one embodiment of the present invention the plant is a production crop plant.

Another embodiment comprises a chimeric protein with i) a recognition element comprising a peptide or protein from a member of the subtilisin family of proteinases, or BPI/LBP sequence; ii) a lysis element comprising a thionin sequence, and a linker that separates i) and ii) such that i) and ii) can fold into an appropriate three-dimensional shape and retain an activity. Subtilisin recognizes the conserved Xf outer-membrane protein MopB whereas BPI/LBP recognizes the conserved LPS moieties of Xf. The linker of one or more embodiments can be an amino acid linker having a length of one or more amino acids but can range in amino acid length, for example, 1-5, 5-10, 10-15, 15-50 and 50-100 or more amino acids. The amino acids that make up the linker may be naturally occurring or non-naturally occurring. Another embodiment comprises a polynucleotide of a nucleic acid sequence encoding the chimeric protein of this embodiment. Another embodiment includes an expression vector comprising this polynucleotide operably linked to a promoter. A genetically altered plant or parts thereof and its progeny comprising this polynucleotide operably linked to a promoter, wherein the plant or parts thereof and its progeny produce the chimeric protein is yet another embodiment. For example, seeds and pollen contain this polynucleotide sequence or a homologue thereof, a genetically altered plant cell comprising this polynucleotide operably linked to a promoter such that the plant cell produces the chimeric protein. Another embodiment comprises a tissue culture comprising a plurality of the genetically altered plant cells. In a further embodiment, the chimeric protein may comprise SEQ ID NOs 4-7 or SEQ ID NOs 30-33 or a sequence with homology thereto. Another embodiment comprises a polynucleotide of a nucleic acid sequence encoding SEQ ID NOs 4-7 or 30-33 or a sequence with homology thereto. A sequence of the disclosure can have about 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to at least one of the SEQ ID Nos. SEQ ID NOs 4-7 or SEQ ID NOs 30-33 or a definsin or subtilisin or a BPT/LBP sequence disclosed herein. Another embodiment includes an expression vector comprising this polynucleotide operably linked to a promoter. A genetically altered plant or parts thereof and its progeny comprising this polynucleotide operably linked to a promoter, wherein the plant or parts thereof and its progeny produce the chimeric protein is yet another embodiment. For example, seeds and pollen contain this polynucleotide sequence or a homologue thereof, a genetically altered plant cell comprising this polynucleotide operably linked to a promoter such that the plant cell produces the chimeric protein. Another embodiment comprises a tissue culture comprising a plurality of the genetically altered plant cells. Another embodiment provides for a method for constructing a genetically altered plant or part thereof having increased resistance to bacterial infections compared to a non-genetically altered plant or part thereof, the method comprising the steps of: introducing a polynucleotide encoding the chimeric protein into a plant or part thereof to provide a genetically altered plant or part thereof, wherein the chimeric protein comprising the linker ranges in length between three amino acids and approximately forty-four amino acids; and selecting a genetically altered plant or part thereof that expresses the chimeric protein, wherein the expressed chimeric protein has anti-bacterial activity; and wherein the genetically altered plant or part thereof has increased resistance to bacterial infections compared to the resistance to bacterial infections of the non-genetically altered plant or part thereof. A polynucleotide encoding the chimeric protein is introduced via introgression or transforming the plant with an expression vector comprising the polynucleotide operably linked to a promoter.

Another embodiment provides for a method of enhancing a wild-type plant's resistance to bacterial diseases comprising transforming a cell from the wild-type plant with a polynucleotide encoding a chimeric protein to generate a transformed plant cell; and growing the transformed plant cell to generate a genetically altered plant wherein the chimeric protein comprises a recognition element, a lysis element; wherein the lysis element comprises a thionin or pro-thionin, and the recognition element comprises Proteinase K or pro-Subtilisin, or subtilisin or pro-subtilisin. A linker may connect the recognition element and the lysis element in a manner that each can fold into its appropriate three-dimensional shape and retain its activity toward a pathogen. The peptide linker ranges in length between three amino acids and approximately forty-four amino acids; wherein the genetically altered plant or part thereof produces the chimeric protein; and wherein the chimeric protein kills bacteria that cause the bacterial diseases; and wherein the genetically altered plant's resistance to the bacterial diseases is greater than the wild-type plant's resistance to the bacterial diseases. Further still, another embodiment comprises a genetically altered host, for example, a plant, (e.g. a grape, or part thereof that is produced by this method). A polynucleotide that encodes for the chimeric protein may be introduced to the plant using an expression vector for *Agrobacterium* for the transformation.

Another embodiment provides for a genetically altered plant or part thereof and its progeny comprising the polynucleotide coding for the compound operably linked to a promoter, wherein the plant or parts thereof and its progeny produce the compound. Further, the genetically altered plant or part thereof wherein its progeny is a seed from the genetically altered plant and/or wherein its parts is pollen from the genetically altered plant and/or wherein its parts are plant cells from the genetically altered plant comprising the polynucleotide operably linked to a promoter, wherein the plant cell produces the compound. Further still, the genetically altered plant or part thereof wherein the plant cell forms a tissue culture.

Another embodiment of the present invention provides for a method for constructing a genetically altered plant or part thereof having increased resistance to infection by a pathogen compared to a non-genetically altered plant or part thereof, the method comprising the steps of introducing a polynucleotide encoding a chimeric protein into a plant or part thereof to provide a genetically altered plant or part thereof. The chimeric protein comprises a recognition element and a lysis element wherein the recognition element is derived from a first protein and the lysis element is derived from a second protein wherein the first protein and the second protein are both endogenous to the plant intended to be treated by the chimeric protein wherein the recognition element binds to the pathogen and the lysis element lyses the pathogen to produce anti-pathogen activity. A genetically altered plant or part thereof that expresses the chimeric protein is selected, wherein the expressed chimeric protein has anti-pathogen activity. The genetically altered plant or part thereof has increased resistance to pathogen infections compared to the resistance to pathogen infections of the non-genetically altered plant or part thereof. For example, introducing the polynucleotide encoding the chimeric protein occurs via introgression or transforming the plant with an expression vector comprising the polynucleotide operably linked to a promoter. The plant that can be produced by this method is a grapevine that produces grapes.

Yet another embodiment provides for a method of enhancing a wild-type plant's resistance to bacterial diseases comprising the steps of transforming a cell from the wild-type plant with a polynucleotide encoding a chimeric protein to generate a transformed plant cell. The transformed plant cell is grown to generate a genetically altered plant wherein a chimeric protein comprises a lysis element and a recognition element. The lysis element comprises a thionin or pro-thionin, and the recognition element comprises Proteinase K or pro-Proteinase K. The genetically altered plant or part thereof produces the chimeric protein. The chimeric protein kills pathogen that cause the pathogen diseases in the host, the genetically altered plant's resistance to the pathogen diseases is greater than the wild-type plant's resistance to the pathogen diseases. The plant that can be produced by this method is, for example, a grapevine that produces grapes.

Another embodiment of the present invention provides for an expression vector for *Agrobacterium*-mediated transformation using the polynucleotide that codes for the chimeric protein.

Another embodiment provides for a composition comprising the chimera protein as described herein. The composition may be used as a topical treatment of plants at risk for infection with *Xylella fastidiosa* (Xf). Further still is an embodiment that provides for a method of treating plants at risk for infection with Xf comprising the steps of applying the composition to the plants at risk of infection with Xf.

Another embodiment provides for a method of treating a production crop plant that is at risk for becoming infected with a pathogen that will harm the production crop plant, the method comprising the steps of applying topically a chimera protein as described herein to the production crop plant at risk of becoming infected.

Another embodiment provides for a method of treating a production crop plant that is at risk for becoming infected with a pathogen that will harm the production crop plant, the method comprising the steps of introducing a sequence that codes for a chimera protein of claim 1 to the production crop plant at risk of becoming infected. For example, the step of introducing includes introducing a sequence that codes for the chimera protein to scion cultivars and root stock cultivars.

Another method provides for using a chimera protein or polynucleotide that codes for the same in a method of conferring resistance against a disease to a production crop scion cultivars or a production crop rootstock cultivars comprising the steps of transforming production crop scion cultivars or production crop rootstock cultivars with a sequence that encodes the chimeric protein as described herein.

Another embodiment of the present invention provides for a transgenic production crop scion cultivar or transgenic production crop rootstock cultivar transformed with a polynucleotide comprising a nucleic acid sequence that encodes for a chimeric protein of claim 1.

Further still, another embodiment comprises a composition comprising a chimeric protein as disclosed herein as a topical treatment of plants at risk for infection with a pathogen for example a Xf and a method of treating plants at risk for infection with the pathogen for example Xf comprising applying the composition to the plants at risk of infection with Xf.

One aspect of one embodiment of the present invention provides for a chimera protein having a recognition element and lysis element from the host proteome. In this embodiment, the recognition element and the lysis element are each specific for the pathogen for example Xf.

One aspect of one embodiment of the present invention provides for transgenic plant lines expressing the chimera protein.

Another aspect of the present invention provides for a transgenic plant line that is pathogen resistant for example Xf resistant.

Another aspect of one embodiment of the present invention is a transgenic plant line that is expected to show high efficacy against a pathogen for example Xf infection and no phytotoxicity Another embodiment provides for the plant to be a grape plant.

Another aspect of the present invention provides for a chimera protein made of grape innate immune proteins useful to create a transgenic plant with innate immunity to Xf caused disease.

Another aspect of the present invention provides for synergy of recognition element and lysis element to facilitate reduction of pathogen load found in a plant infected with the pathogen. In another aspect of the present invention, synergy of recognition element and lysis element facilitates clearing or reducing a pathogen or a pathogen load found in a plant infected with the pathogen. (Proc Natl Acad Sci USA. 2012 Mar. 6; 109(10):3721-5)

Another aspect of the present invention provides for a method of enhancing a plant's resistance to pathogen diseases by transforming a plant with a chimera protein introduced to the plant (or otherwise altering the DNA of plant to express the chimeric protein) with one or more polynucleotides encoding one or more chimeric proteins described herein such that the plant containing the heterologous DNA produces the chimeric protein, and the chimeric protein kills pathogen for example a bacteria that causes harm to the plant after the bacteria infect the plant.

In reference to any embodiment, identity can be calculated by known methods. Identity, or homology, percentages as mentioned herein are those that can be calculated with the Blast program or GAP program, running under GCG (Genetics Computer Group Inc., Madison, Wis., USA). Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Nat. Acad Sci. USA 85:2444, 1988; Higgins & Sharp, Gene, 73:23744, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth Mol. Bio. 24:307-31, 1994. Altschul et al., J. Mol. Biol. 215:403-10, 1990, presents a detailed consideration of sequence alignment methods and homology calculations.

Objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 1. A typical three-layers membrane of a gram-negative bacterium such as Xf is shown. The outer-membrane protein mopB and LPS are possible recognition targets. mopB is targeted by grape subtilisin where LPS is targeted by grape BPI/LBP. Grape gamma thionins with selectivity for gram-negative bacteria such as Xf are chosen as lysis elements/domain.

FIG. 2A Defensin on the N-terminal and subtilisin on the C-terminal. FIG. 2B subtilisin on the N-terminal and Defensin on the C-terminal.

FIG. 3A Defensin on the N-terminal and BPI/LBP on the C-terminal. FIG. 3B BPI/LBP on the N-terminal and Defensin on the C-terminal.

FIG. 4. Amino acid sequences of the chimeras shown in FIGS. 2 and 3 are illustrated in ribbon structure. Subtilisin has been chosen as the recognition (cleavage) element/domain over HNE due to its higher cleavage activity on mopB. BPI/LBP family proteins are conserved in human, animal, and plant. Grape BPI/LBP consists of two similar elements/domains that can bind LPS and penetrate outer-membrane of gram-negative bacteria. They are joined by a proline-rich linker. One such BPI/LBP element/domain and the same linker is chosen when BPI/LBP is on the N-terminal of the chimera. When grape defensin on the N-terminal of the chimera, GSTAPPA (SEQ ID NO 18) linker is used to join both BPI/LBP and subtilisin. We have also designed chimeras by extending the grape defensin sequence beyond the last cysteine by VFDEK (SEQ ID NO 29) to increase activity and lower toxicity.

DETAILED DESCRIPTION OF THE INVENTION

Figure 2:
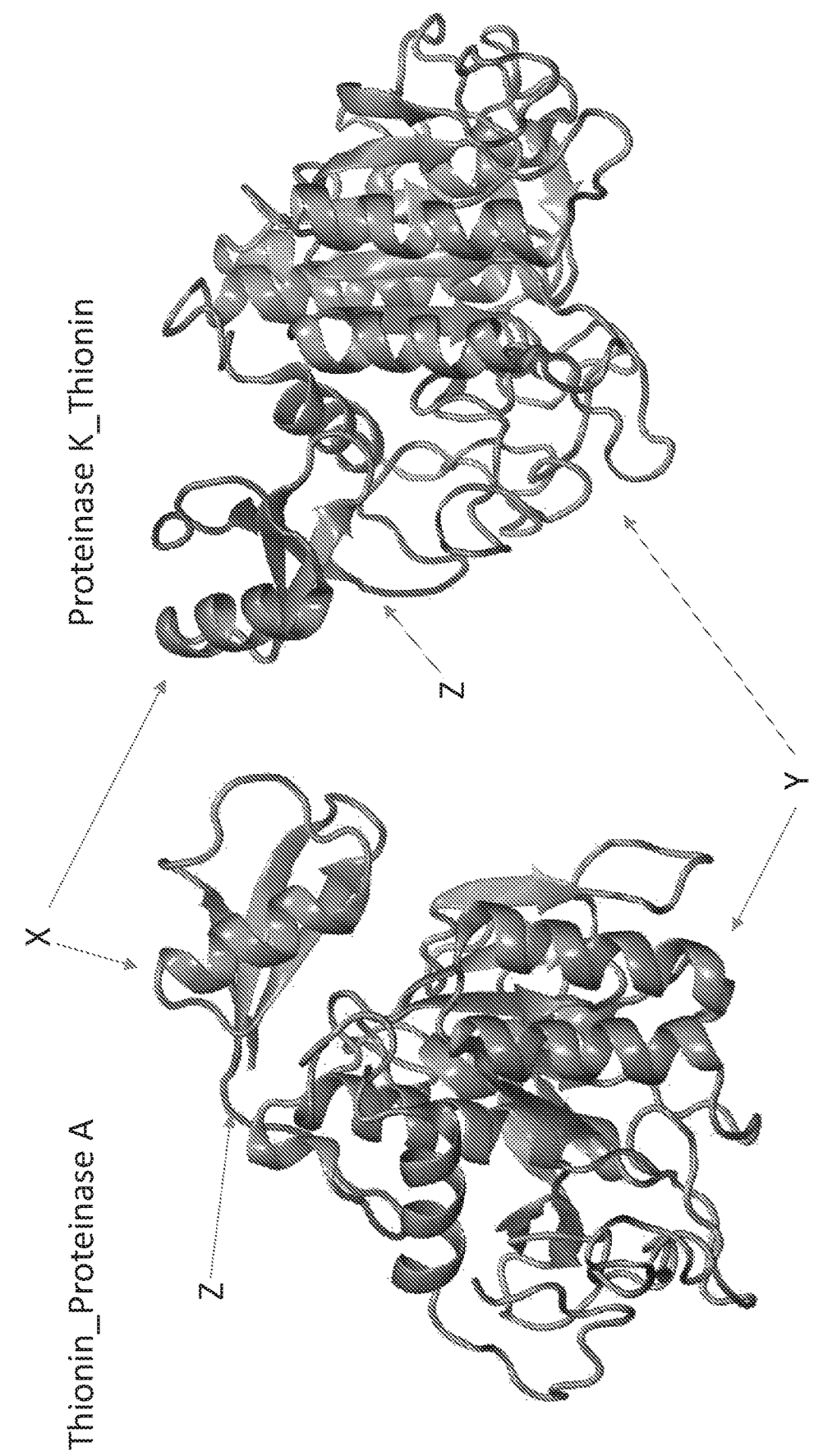
FIG. 2. Chimeras according to one embodiment of the present invention comprise grape subtilisin and thionin. Codes: X=subtilisin; Y=defensin; Z=linker.

One embodiment of the present invention provides for treatment of host diseases caused by pathogens such as bacteria for example the xylem-limited bacteria *Xylella fastidiosa* (Xf) that infects hosts such as grapevines to cause Pierces' disease and *Xanthamonas* and *Pseudomonas* strains that cause spot and speck in tomato. Because this invention involves production of genetically altered hosts and compositions for use in transforming hosts and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

In one embodiment of the present invention, a chimeric protein is a non-naturally occurring sequence having a recognition element that is derived from a first peptide or protein sequence found in a host to be treated with the chimeric protein and also included in the chimeric protein is a lysis element that is derived from a second peptide or protein found in the host to be treated with the chimeric protein, wherein individually the first peptide or protein and the second peptide or protein provide to the host anti-pathogen activity and wherein the first peptide or protein and the second peptide or protein bind to different targets on the pathogen.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because the amino acid sequences of D4E1, thionin, pro-thionin, optimized thionin, optimized pro-thionin, linker 1, linker 2, linker 3, linker 4, linker 5, linker 6, and the chimeric proteins are described, one can chemically synthesize a polynucleotide which encodes these polypeptides/chimeric proteins. Because of the degeneracy of nucleic acid codons, one can use various different polynucleotides to encode identical polypeptides. Table 2, infra, contains information about which nucleic acid codons encode which amino acids.

TABLE 1

Amino acid Nucleic acid codons

| Amino Acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 3 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 2

Amino Acid Conservative Substitute

| Amino Acid | Conservative Substitute |
|---|---|
| Ala | Gly, Ser |
| Arg | His, Lys |
| Asn | Asp, Gln, His |

TABLE 2-continued

Amino Acid Conservative Substitute

| Amino Acid | Conservative Substitute |
|---|---|
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, Tetrahedron Letts. 22:1859-1862 (1981), or using an automated synthesizer, as described in Van Devanter et al., Nucleic Acids Res. 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, J. Chrom. 255:137-149 (1983).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native/endogenous nucleic acid or protein, or that the cell is derived from a cell so modified. Thus, for example, recombinant cells may express genes that are not found within the native (non-recombinant or wild-type) form of the cell or express native genes, proteins or portions thereof that are otherwise abnormally expressed—over-expressed, under-expressed or not expressed at all for example a peptide or protein of the form of the chimeric protein or a nucleotide sequence coding for the chimeric protein sequence.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides, or the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed, transfected or transferred into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Transformation and generation of genetically altered monocotyledonous and dicotyledonous plant cells is well known in the art. See, e.g., Weising, et al., Ann. Rev. Genet. 22:421-477 (1988); U.S. Pat. No. 5,679,558; Agrobacterium Protocols, ed: Gartland, Humana Press Inc. (1995); and Wang, et al. Acta Hort. 461:401-408 (1998). The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see, e.g., EP 295959); techniques of electroporation (see, e.g., Fromm et al., Nature 319:791 (1986)); and high-velocity ballistic bombardment with metal particles coated with the nucleic acid constructs (see, e.g., Kline, et al., Nature 327:70 (1987)

and U.S. Pat. No. 4,945,050). Specific methods to transform heterologous genes into commercially important crops (to make genetically altered plants) are published for rapeseed (De Block, et al., Plant Physiol. 91:694-701 (1989)); sunflower (Everett, et al., Bio/Technology 5:1201 (1987)); soybean (McCabe, et al., Bio/Technology 6:923 (1988), Hinchee, et al., Bio/Technology 6:915 (1988), Chee, et al., Plant Physiol. 91:1212-1218 (1989), and Christou, et al., Proc. Natl. Acad. Sci USA 86:7500-7504 (1989)); rice (Hiei, et al., Plant J. 6:271-282 (1994)), and corn (Gordon-Kamm, et al., Plant Cell 2:603-618 (1990), and Fromm, et al., Biotechnology 8:833-839 (1990)). Other known methods are disclosed in U.S. Pat. Nos. 5,597,945; 5,589,615; 5,750,871; 5,268,526; 5,262,316; and 5,569,831.

One exemplary method includes employing *Agrobacterium tumefaciens* or *Agrobacterium rhizogenes* as the transforming agent to transfer heterologous DNA into the plant. *Agrobacterium tumefaciens*-meditated transformation techniques are well described in the scientific literature. See, e.g., Horsch, et al. Science 233:496-498 (1984), and Fraley, et al. Proc. Natl. Acad. Sci. USA 80:4803 (1983). Typically, a plant cell, an explant, a meristem or a seed is infected with *Agrobacterium tumefaciens* transformed with the expression vector/construct which contains the heterologous nucleic acid operably linked to a promoter. Under appropriate conditions known in the art, the transformed plant cells are grown to form shoots, roots, and develop further into genetically altered plants. In some embodiments, the heterologous nucleic acid can be introduced into plant cells, by means of the Ti plasmid of *Agrobacterium tumefaciens*. The Ti plasmid is transmitted to plant cells upon infection by *Agrobacterium tumefaciens*, and is stably integrated into the plant genome. See, e.g., Horsch, et al. (1984), and Fraley, et al. (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, in Handbook of Plant Cell Culture, pp. 124-176, MacMillan Publishing Company, New York, 1983; and Binding, Regeneration of Plants, in Plant Protoplasts, pp. 21-73, CRC Press, Boca Raton, 1985. Regeneration can also be obtained from plant callus, explants, organs, or parts thereof. Such regeneration techniques are described generally in Klee, et al., Ann. Rev. of Plant Phys. 38:467-486 (1987).

This invention utilizes routine techniques in the field of molecular biology. Basic texts disclosing the general methods of use in this invention include Green and Sambrook, 4th ed. 2012, Cold Spring Harbor Laboratory; Kriegler, Gene Transfer and Expression: A Laboratory Manual (1993); and Ausubel et al., eds., Current Protocols in Molecular Biology, 1994-current, John Wiley & Sons. Unless otherwise noted, technical terms are used according to conventional usage. Definitions of common terms in molecular biology maybe found in e.g., Benjamin Lewin, Genes IX, published by Oxford University Press, 2007 (ISBN 0763740632); Krebs, et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants including eudicots. It includes plants of a variety of ploidy levels, including aneuploid, polyploid, diploid, haploid and hemizygous. The genetically altered plants described herein can be monocot crops, such as, sorghum, maize, wheat, rice, barley, oats, rye, millet, and triticale. The genetically altered plants described herein can also be dicot crops, such as apple, grape, pear, peach, plum, orange, lemon, lime, grapefruit, pomegranate, olive, peanut, tobacco, etc. Also, the genetically altered plants (or plants with altered genomic DNA) can be horticultural plants such as rose, marigold, primrose, dogwood, pansy, geranium, etc. In some embodiments, the genetically altered plants are citrus plants. In other embodiments, the genetically altered plants are *N. benthamiana* or tobacco plants.

Once a genetically altered plant has been generated, one can breed it with a wild-type plant and screen for heterozygous F1 generation plants containing the genetic change present in the parent genetically altered plant. Then F2 generation plants can be generated which are homozygous for the genetic alteration. These heterozygous F1 generation plants and homozygous F2 plants, progeny of the original genetically altered plant, are considered genetically altered plants, having the altered genomic material from the genetically altered parent plant.

After one obtains a genetically altered plant expressing the chimeric protein, one can efficiently breed the genetically altered plant with other plants containing desired traits. One can use molecular markers (i.e., polynucleotide probes) based on the sequence of the chimeric protein as described above to determine which offspring of crosses between the genetically altered plant and the other plant have the polynucleotide encoding the chimeric protein. This process is known as Marker Assisted Rapid Trait Introgression (MARTI). Briefly, MARTI involves (1) crossing the genetically altered plant with a plant line having desired phenotype/genotype ("elite parent") for introgression to obtain F1 offspring. The F1 generation is heterozygous for chimeric protein trait. (2) Next, an F1 plant is be backcrossed to the elite parent, producing BC1F1 which genetically produces 50% wild-type and 50% heterozygote chimeric protein. (3) PCR using the polynucleotide probe is performed to select the heterozygote genetically altered plants containing polynucleotide encoding the chimeric protein. (4) Selected heterozygotes are then backcrossed to the elite parent to perform further introgression. (5) This process of MARTI is performed for another four cycles. (6) Next, the heterozygote genetically altered plant is self-pollinated by bagging to produce BC6F2 generation. The BC6F2 generation produces a phenotypic segregation ratio of 3 wild-type parent plants to 1 chimeric protein genetically altered plant. (7) One selects genetically altered chimeric protein plants at the BC6F2 generation at the seedling stage using PCR with the polynucleotide probe and can optionally be combined with phenotypic selection at maturity. These cycles of crossing and selection can be achieved in a span of 2 to 2.5 years (depending on the plant), as compared to many more years for conventional backcrossing introgression method now in use. Thus, the application of MARTI using PCR with a polynucleotide probe significantly reduces the time to introgress the chimeric protein genetic alteration into elite lines for producing commercial hybrids. The final product is an inbred plant line almost identical (99%) to the original elite in-bred parent plant that is the homozygous for the polynucleotide encoding the chimeric protein.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having described the invention in general terms, below are examples illustrating the generation and efficacy of the invention.

Referring to FIG. 1, the recognition sites MopB and Lipopolysaccharide on the surface of the gram-negative Xf are identified.

Figure 5:
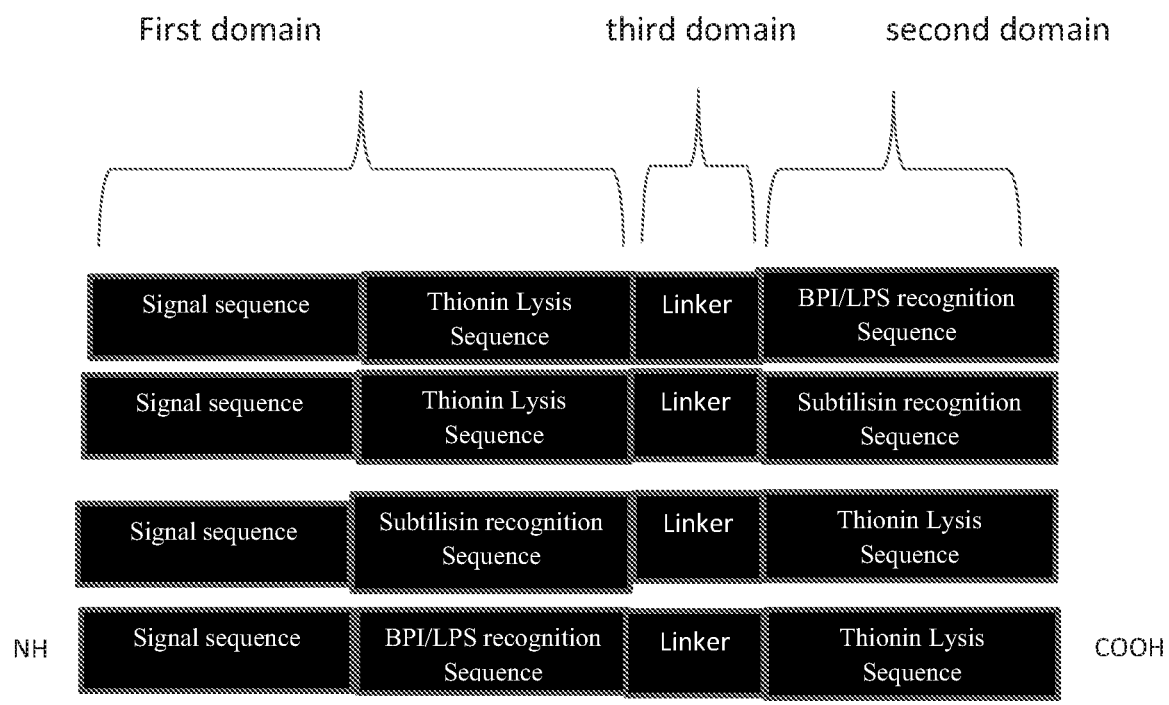
FIG. 5. Chimera peptides are illustrated according to one embodiment of the present invention having a first domain, second domain and a third domain.

Referring now to FIG. 5, a chimera protein is illustrated having a recognition element to target both mopB and lipopolysaccharide (LPS) on the Xf membrane. The recognition element can be located at the amine (N)-terminus of the protein chimera or at the carboxy (C)-terminus of the chimera or therebetween. The recognition element is joined to a grape defensin (thionin) to form the chimera. The defensin can be located at either the amine terminus or the carboxy terminus or at a position therebetween and may be connected to the recognition element by a linker. The recognition element can be a subtilisin which targets mopB since it has higher cleavage activity on mopB than HNE. In one embodiment, the subtilisin is a homolog of the plant which will be treated with the chimera rather than from a different species or a human homolog. The recognition element can also be the bactericidal permeability-increasing protein (BPI)/Lipopolysaccharide-binding protein (LBP) protein. The BPI/LBP can be a homolog of the plant to be treated for example grape with the recognition element having specificity for Xf LPS. In addition to binding to LPS, BPI/LBP can increase the permeability of the chimera thereby also increasing the membrane pore forming ability of the defensin or lysis element. In one embodiment, at the amine terminus is a signaling sequence that facilitates the secretion of the chimera in the xylem (the site of Xf colonization). The linker can be a plurality of amino acids or other linker type. The linker can be between 2-10, 10-20, 20-40, 40-100, or 100-200 or more amino acids. Alternatively, the linker can be a non-amino acid linker.

Referring now to FIG. 2 two types of protein chimeras are illustrated in ribbon structure. Panel A illustrates a chimera having defensin on the N-terminal and subtilisin on the C-terminal. Panel B illustrates a chimera with subtilisin on the N-terminal and defensin on the C-terminal. In one embodiment, the subtilisin is a grape homolog which belongs to the subtilisin family.

Figure 3:
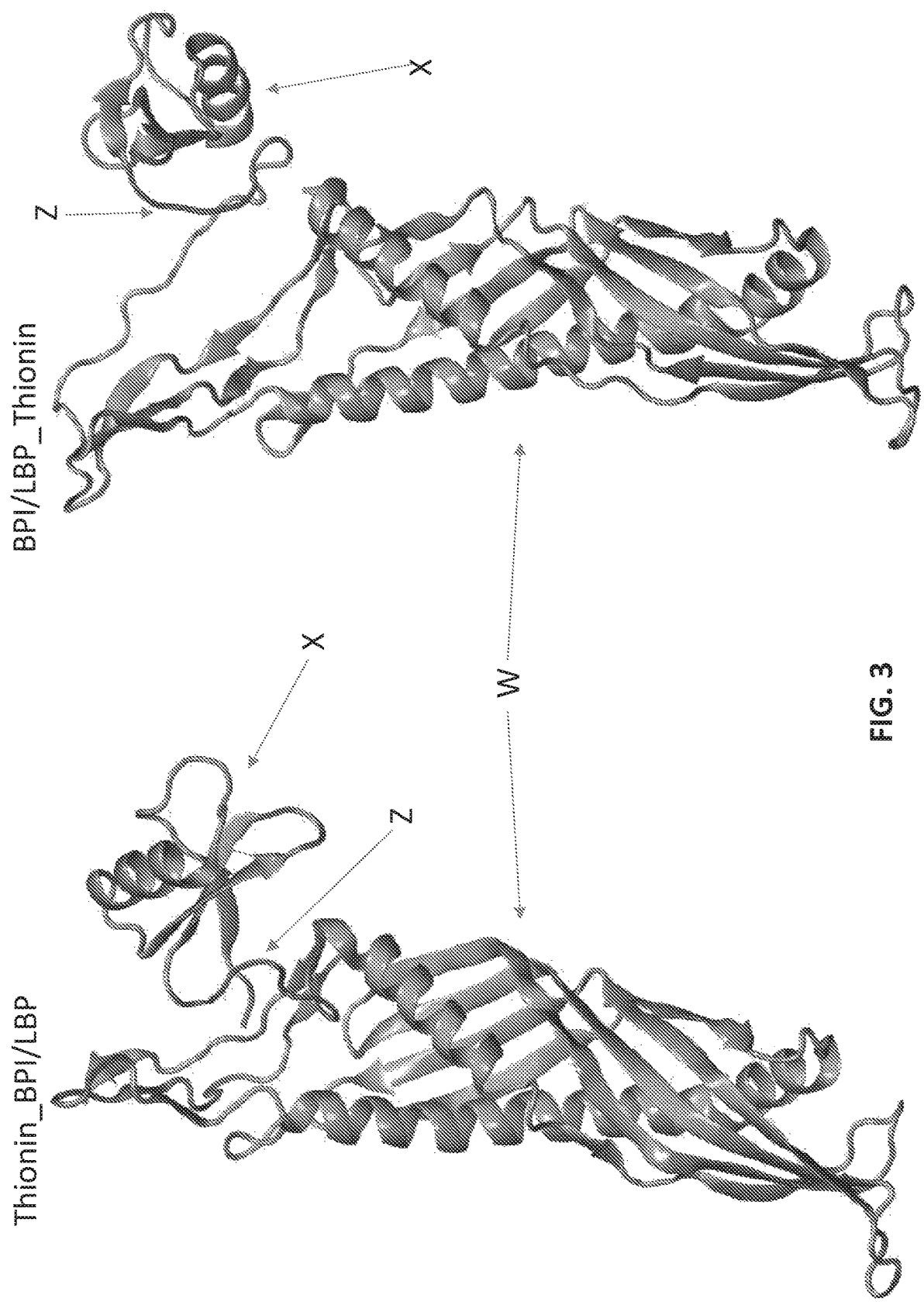
FIG. 3. Chimeras according to one embodiment of the present invention comprise grape BPI/LBP and thionin. Codes: W=BPI/LBP; X=defensin; Z=linker.

Referring now to FIG. 3 a ribbon structure of a protein chimera is illustrated. Panel A illustrates a chimera with defensin on the N-terminal and BPI/LBP on the C-terminal. Panel B illustrates a chimera with BPI/LBP on the N-terminal and defensin on the C-terminal.

Referring now to FIG. 4, the amino acid sequence of four different embodiments of chimera proteins are illustrated. Note that in addition to the sequences of the active chimera with recognition element, linker, and lysis element, the upstream signal sequence is also included in these embodiments. The signal sequence facilitates the secretion of the chimera in the xylem (the site of Xf colonization) when a nucleotide sequence encoding for the chimera is introduced to the plant. In one embodiment, both the recognition element (BPI/LBP and subtilisin) and lysis element (defensin) are chosen from the host proteome for example the grape proteome. The chimera proteins as described herein are expected to be more active than HNE and insect Cecropin B chimera proteins previously described. One aspect of utilizing a recognition element and a lysis element is to provide a protein chimera having little or no toxicity to the plant to be treated with the chimeric protein and will also allow for both *Agrobacterium*-mediated and precision plant breeding by CRISPR/CAS thereby making the invention more grower and consumer friendly. When the sequence corresponding to a thionin, subtilisin or BPI/LBP is located at the amino terminus of the chimeric protein, it may be encoded as a pro-protein (pro-thionin or pro-subtilisin or pro-BPI/LBP) which may contain an amino acid signal sequence (the exact number of amino acids in the signal sequence can vary by organism). The signal sequence assists in the trafficking of the chimeric protein to the endoplasmic reticulum or a cellular vesicle. Not wishing to be bound to a particular hypothesis, it is believed that the signal sequence is cleaved off pro-protein prior to, during, or after passage of pro-protein through the lipid membrane to yield mature protein. See, Romero, et al., Eur. J. Biochem. 243:202-8 (1997). When thionin, subtilisin or BPI/LBP is located at the carboxyl terminus of the chimeric protein, thionin, subtilisin or BPI/LBP does not contain an amino acid signal sequence. However, the chimeric protein still can contain an amino acid signal sequence at the amino terminus of the chimeric protein as described below. The thionin (or pro-thionin) can be a thionin (or pro-thionin) that exists in a plant (and more specifically in a grape plant), or an optimized thionin (or optimized pro-thionin) as described below. The subtilisin (or pro-subtilisin) can be a subtilisin (or pro-subtilisin) that exists in a plant (and more specifically in a grape plant), or an optimized subtilisin (or pro-subtilisin) as described below. The BPI/LBP (or pro-BPI/LBP) can be a BPI/LBP (or pro-BPI/LBP) that exists in a plant (and more specifically in a grape plant), or an optimized BPI/LBP (or pro-BPI/LBP) as described below. The peptide linker, can be a selected from SEQ ID NOs: 17-23 and 27-28 or a variant thereof or a non-amino acid linker.

TABLE 3

Sequence Listing

| SEQ ID NO | ID | Name | AA/nucleotide |
|---|---|---|---|
| 1 | XM_0022 80906.3 | Subtilisin stb6.1 or subtilisin (vitis vinifera) The domain 204-469 amino acid of the 1046 amino acid long protein Subtilisin Sequence *from Human neutrophil elastase NM_001972.3 | 1 MTLGRRLACL FLACVLPALL LGGTASASER GLWEKGYTGA KVKMAIFDTG IRANHPHFRN<br>61 IKERTNWTNE DTLNDNLGHG TFVAGVIAGQ YDECLGFAPD TEIYAFRVFT DAQVSYTSWF<br>121 LDAFNYAIAT NMDVLNLSIG GPDYLDLPVF EKVWELTANN IIMVSAIGND GPLYGTLNNP<br>181 ADQSDVIGVI DYGDHIASFS SRGMSTWEIP HGYGRVKPDV VAYGREIMGS SISANCKSLS<br>241 GTSVASPVVA GVVCLLVSVI PEHDRKNILN PASMKQALVE GAARLPDANM YEQGAGR |
| 2 | XM_0106 54727.2 | Gamma thionin (vitis vinifera) | 1 MERKSLGFFF FLLLILLASQ MVVPSEA RVC ESQSHKFEGA CMGDHNCALV CRNEGFSGGK<br>61 CKGLRRRCFC TKLCVFDEK |
| 3 | XP_0022 72020.1 | BPI/LBP domain (vitis vinifera) | 1 MRPSVLVIFI AFLLFTPSQA HLKSTESSFI SILISSQGLD FIKNLLITKA ISSLTPLQLP<br>61 QIKKSVKIPF LGRVDIAFSN ITIYHIDVSS SNIAPGDTGV AIIASGTTCN LSMNWHYSYN<br>121 TWFVPVEISD SGTAQVQVEG MEVGLTLGLE NREGSMKLSA KDCGCYVEDI SIKLDGGASW<br>181 LYQGVVDAFE EQIGSAVEST ITKKLKEGII KLDSFLQALP KEIPVDNIAS LNVTFVNDPL<br>241 LSNSSIGFDI NGLFT RANAT TLPKYYQNSR HPVSCTDPSK |
| 4 | | Thionin-linker-BPI/LBP (vitis vinifera) | 1 MERKSLGFFF FLLLILLASQ MVVPSEA RVC ESQSHKFEGA CMGDHNCALV CRNEGFSGGK CKGLRRRCFC TKLCVFDEK GSTAPPA SSQG LDFIKNLLIT KAISSLTPLQ LPQIKKSVKI PFLGRVDIAF SNITIYHIDV SSSNIAPGDT GVAIIASGTT CNLSMNWHYS YNTWFVPVEI SDSGTAQVQV EGMEVGLTLG LENREGSMKL SAKDCGCYVE DISIKLDGGA SWLYQGVVDA<br>241 FEEQIGSAVE STITKKLKEG IIKLDSFLQA LPKEIPVDNI ASLNVTFVND PLLSNSSIGF<br>301 DINGLFT |
| 5 | | BPI/LBP-linker-Thionin (vitis vinifera) | 1 MRPSVLVIFI AFLLFTPSQA HLKSTESSFI SILISSQGLD FIKNLLITKA ISSLTPLQLP<br>61 QIKKSVKIPF LGRVDIAFSN ITIYHIDVSS SNIAPGDTGV AIIASGTTCN LSMNWHYSYN<br>121 TWFVPVEISD SGTAQVQVEG MEVGLTLGLE NREGSMKLSA KDCGCYVEDI SIKLDGGASW<br>181 LYQGVVDAFE EQIGSAVEST ITKKLKEGII KLDSFLQALP KEIPVDNIAS LNVTFVNDPL<br>241 LSNSSIGFDI NGLFT RANAT TLPKYYQNSR HPVSCTDPSK RVCESQSHKF EGACMGDHNC<br>301 ALVCRNEGFS GGKCKGLRRR CFCTKLC VFDEK |

TABLE 3-continued

| SEQ ID NO | ID | Name | AA/nucleotide |
|---|---|---|---|
| 6 | | Thionin-Linker-Subtilisin (vitis vinifera) | 1 MERKSLGFFF FLLLILLASQ MVVPSEARVS ESQSHKFEGA CMGDHNCALV CRNEGFSGGK 61 CKGLRRRCFC TKLCVFDEKG STAPPA RGLW EKGYTGAKVK MAIFDTGIRA NHPHFRNIKE RTNWTNEDTL NDNLGHGTFV AGVIAGQYDE CLGFAPDTEI YAFRVFTDAQ VSYTSWFLDA FNYAIATNMD VLNLSIGGPD YLDLPFVEKV WELTANNIIM VSAIGNDGPL YGTLNNPADQ SDVIGVIDYG DHIASFSSRG MSTWEIPHGY GRVKPDVVAY GREIMGSSIS ANCKSLSGTS VASPVVAGVV CLLVSVIPEH DRKNILNPAS MKQALVEGAA RLPDANMYEQ GAGR |
| 7 | | Subtilisin-linker-Thionin (vitis vinifera) | 1 MTLGRRLACL FLACVLPALL LGGTALASER GLWEKGYTGA KVKMAIFDTG IRANHPHFRN 61 IKERTNWTNE DTLNDNLGHG TFVAGVIAGQ YDECLGFAPD TEIYAFRVFT DAQVSYTSWF 121 LDAFNYAIAT NMDVLNLSIG GPDYLDLPFV EKVWELTANN IIMVSAIGND GPLYGTLNNP 181 ADQSDVIGVI DYGDHIASFS SRGMSTWEIP HGYGRVKPDV VAYGREIMGS SISANCKSLS 241 GTSVASPVVA GVVCLLVSVI PEHDRKNILN PASMKQALVE GAARLPDANM YEQGAGRGST 301 APPARVCESQ SHKFEGACMG DHNCALVCRN EGFSGGKCKG LRRRCFCTKL CVFDEK |
| 8 | FN595233.1 | Substilisin (or subtilase) domain (showing 27% identity with sequence 1) from a 822 amino acid long protein (vitis vinifera) | 1 MIYAFRITLI YTYSNSINGF SASLTLSELE ALKKSPGYLS STPDQF 47 VQPH TTRSHEFLGL 61 RRGSGAWTAS NYGNGVIIGL VDSGIWPESA SFKDEGMGKP PPRWKGACVA DANFTSSMCN 121 NKIIGARYYN RGFLAKYPDE TISMNSSRDS EGHGTHTSST AAGAFVEGVS YFGYANGTAA 181 GMAPRAWIAV YKAIWSGRIA QSDALAAIDQ AIEDGVDILS LSFSFGNNSL NLNPISIACF 241 TAMEKGIFVA ASAGNDGNAF GTLSNGEPWV TTVGAEMGTK PAPMVDIYSS RGPFIQCPNV 301 LKPDILAPGT SVLAAWPSNT PVSDNFYHQW YSDFNVLSGT SMATAHVAGV AALVKAVHPN 361 WSPAAIRSAL MTTANTLDNT |
| 9 | XM_002274317.3 55% identity with sequence 2 | Gamma thionin (vitis vinifera) | 1 MKGSQRLFSA FLLVILLFMA TEMGPMVAEA RTCESQSHRF KGTCVRQSNC AAVCQTEGFH 61 GGNCRGFRRR CFCTKHC |
| 10 | XM_002263344.4 64% identity with sequence 2 | Gamma thionin (vitis vinifera) | 1 MKHLEDLKFK KKKMTKKKEE AMEKKSPLGL TFLLLLLLMA SQETEA RLCE SQSHWFRGVC 61 VSNHNCAVVC RNEHFVGGRC RGFRRRCFCT RNC |

TABLE 3-continued

Sequence Listing

| SEQ ID NO | ID | Name | AA/nucleotide |
|---|---|---|---|
| 11 | XM 0022 77107.4 59% identity with sequence 3 | BPI/LBP domain (vitis vinifera) | 1 MGLSSNLMAP AAFFIVLALF SVP TDAQIKS DEGFISVFIS SKGLGFVKDL LMHKAVSSLT<br>61 PIEIQPIEKI VKIPLVGQVD ILLSNITILS VGVGTSYVSS GGAGVVIVAS GGTANMSMNW<br>121 KYSYDTWLFP ISDKGAASVL VEGMAMELTL GLKDQNGTLS LSLLDWGCFV KDIFVKLDGG<br>181 ATWFYQGLVD AFKEQIASAV EDSVSKRIRE GIIKLDSLLQ SVPKEIPVDH VAALNVTFVK<br>241 DPVSSNSSID FEINGLFT AK DGIPAPTNYH KKHRAPVSCT GPAKM |
| 12 | XM 0022 77107.4 59% identity with sequence 3 | BPI/LBP domain (vitis vinifera) | 1 MGLSSNLMAP AAFFIVLALF SVP TDAQIKS DEGFISVFIS SKGLGFVKDL LMHKAVSSLT<br>61 PIEIQPIEKI VKIPLVGQVD ILLSNITILS VGVGTSYVSS GGAGVVIVAS GGTANMSMNW<br>121 KYSYDTWLFP ISDKGAASVL VEGMAMELTL GLKDQNGTLS LSLLDWGCFV KDIFVKLDGG<br>181 ATWFYQGLVD AFKEQIASAV EDSVSKRIRE GIIKLDSLLQ SVPKEIPVDH VAALNVTFVK<br>241 DPVSSNSSID FEINGLFT |
| 13 | | Endogenous subtilisin stb6.1 or subtilisin (vitis vinifera) | 1 MVASRSSFAY YFLLVVSFC LLRLGDRINY ETLTLTPPRT |
| 14 | (XM 0022 80906.3) | Subtilisin stb6.1 or subtilisin (vitis vinifera) | 1 GLWEKGYTGA KVKMAIFDTG IRANHPHFRN<br>61 IKERTNWTNE DTLNDNLGHG TFVAGVIAGQ YDECLGFAPD TEIYAFRVFT DAQVSYTSWF<br>121 LDAFNYAIAT NMDVLNLSIG GPDYLDLPFV EKVWELTANN IIMVSAIGND GPLYGTLNNP<br>181 ADQSDVIGVI DYGDHIASFS SRGMSTWEIP HGYGRVKPDV VAYGREIMGS SISANCKSLS<br>241 GTSVASPVVA GVVCLLVSVI PEHDRKNILN PASMKQALVE GAARLPDANM YEQGAGR |
| 15 | XM 0106 54727.2 | Gamma thionin (vitis vinifera) | 1 *RVC ESQSHKFEGA CMGDHNCALV CRNEGFSGGK*<br>*61 CKGLRRRCFC TKLCVFDEK* |
| 16 | XP 0022 72020.1 | BPI/LBP (vitis vinifera) | 1 SSQG LDFIKNLLIT KAISSLTPLQ LPQIKKSVKI<br>PFLGRVDIAF SNITIYHIDV SSSNIAPGDT GVAIIASGTT CNLSMNWHYS YNTWFVPVEI SDSGTAQVQV EGMEVGLTLG LENREGSMKL SAKDCGCYVE DISIKLDGGA SWLYQGVVDA<br>241 FEEQIGSAVE STITKKLKEG IIKLDSFLQA LPKEIPVDNI ASLNVTFVND PLLSNSSIGF<br>301 DINGLFT |
| 17 | | Linker | AKDGIPAPTNYHKKHRAPVSCTGPAKM |
| 18 | | Linker | GSTAPPA |
| 19 | | Linker | RANATTLPKYYQNSRHPVSCTDPSK |
| | | Linker | RW |
| | | Linker | SRD |
| 20 | | Linker | GSTAPPAGSTAPPA |
| 21 | | Linker | QASHTCVCEFNCAPL |
| 22 | | Linker | ARKKASIPNYYNSNLQPPVF CSDQSKM |
| 23 | | Linker | YEQGAGRGSTAPPA |
| 27 | | Linker | GSTA |
| 28 | | Linker | GGGSGGGTDGR |
| 24 | | Signal Sequence | MVASRSSFAY YFLLVLVSFC LLRLGDRINY ETLTLTPPRT |

TABLE 3-continued

| SEQ ID NO | ID | Name | AA/nucleotide |
|---|---|---|---|
| 25 | | Signal Sequence | MGKHHVTLCC VVFAVLCLAS SLAQA |
| 26 | | Signal Sequence | MELKFSTFLSLTLLFSSVLNPALS |
| 29 | | Artificial sequence | VFDEK |
| 30 | | BPI/LBP_Thionin Mature chimera protein devoid of signal sequence | SQGLD FIKNLLITKA ISSLTPLQLPQIKKSVKIPF LGRVDIAFSN ITIYHIDVSS SNIAPGDTGV AIIASGTTCN LSMNWHYSYNTWFVPVEISD SGTAQVQVEG MEVGLTLGLE NREGSMKLSA KDCGCYVEDI SIKLDGGASWLYQGVVDAFE EQIGSAVEST ITKKLKEGII KLDSFLQALP KEIPVDNIAS LNVTFVNDPL<br><br>LSNSSIGFDI NGLFTRANAT TLPKYYQNSRHPVSCTDPSK RVCESQSHKF EGACMGDHNCALVCRNEGFS GGKCKGLRRR CFCTKLCVFD EK |
| 31 | | Thionin_BPI/LBP Mature chimera protein devoid of signal sequence | RVC ESQSHKFEGA CMGDHNCALV CRNEGFSGGK CKGLRRRCFC TKLCVFDEKG STAPPASSQG LDFIKNLLIT KAISSLTPLQ LPQIKKSVKIPFLGRVDIAFSNITI YHIDVSSSNI APGDTGVAII ASGTTCNLSM NWHYSYNTWF VPVEISDSGTAQVQVEGMEVGLTLGLENRE GSMKLSAKDC GCYVEDISIK LDGGASWLYQ GVVDAFEEQIGSAVESTITK KLKEGIIKLD SFLQALPKEI PVDNIASLNV TFVNDPLLSN SSIGFDINGL |
| 32 | | Thionin_Subtilisin Mature chimera protein devoid of signal sequence | RVC ESQSHKFEGA CMGDHNCALV CRNEGFSGGK<br><br>CKGLRRRCFC TKLCVFDEKG STAPPARGLWEKGYT GAKVKMAIFD TGIRANHPHF RNIKERTNWT<br><br>NEDTLNDNLG HGTFVAGVIA GQYDECLGFA PDTEIYAFRV FTDAQVSYTS WFLDAFNYAI<br><br>ATNMDVLNLS IGGPDYLDLP FVEKVWELTA NNIIMVSAIG NDGPLYGTLN NPADQSDVIG<br><br>VIDYGDHIAS FSSRGMSTWE IPHGYGRVKP DVVAYGREIM GSSISANCKS LSGTSVASPV<br><br>VAGVVCLLVS VIPEHDRKNI LNPASMKQAL VEGAARLPDA NMYEQGAGR |
| 33 | | Subtilisin_Thionin Mature chimera protein devoid of signal sequence | 1 GLWEKGYTGA KVKMAIFDTG IRANHPHFRN IKERTNWTNE DTLNDNLGHG TFVAGVIAGQ YDECLGFAPD TEIYAFRVFT DAQVSYTSWF LDAFNYAIAT NMDVLNLSIG GPDYLDLPFV EKVWELTANN IIMVSAIGND GPLYGTLNNP<br><br>ADQSDVIGVI DYGDHIASFS SRGMSTWEIP HGYGRVKPDV VAYGREIMGS SISANCKSLS<br><br>GTSVASPVVA GVVCLLVSVI PEHDRKNILN PASMKQALVE GAARLPDANM YEQGAGRGST<br><br>APPARVCESQ SHKFEGACMG DHNCALVCRN EGFSGGKCKG LRRRCFCTKL CVFDEK |

TABLE 3-continued

Sequence Listing

| SEQ ID NO | ID | Name | AA/nucleotide |
|---|---|---|---|
| 34 | | Grape: BPI/LBP | 1 MRPSVLVIFI AFLLFTPSQA HLKSTESSFI SILISSQGLD FIKNLLITKA ISSLTPLQLP<br>61 QIKKSVKIPF LGRVDIAFSN ITIYHIDVSS SNIAPGDTGV AIIASGTTCN LSMNWHYSYN<br>121 TWFVPVEISD SGTAQVQVEG MEVGLTLGLE NREGSMKLSA KDCGCYVEDI SIKLDGGASW<br>181 LYQGVVDAFE EQIGSAVEST ITKKLKEGII KLDSFLQALP KEIPVDNIAS LNVTFVNDPL<br>241 LSNSSIGFDI NGLFT |
| 35 | | Grape: Thionin | 1 MERKSLGFFF FLLLILLASQ MVVPSEA*RVC ESQSHKFEGA CMGDHNCALV CRNEGFSGGK*<br>61 *CKGLRRRCFC TKLCVFDEK* |
| 36 | | Grape: Subtilisin | 1 MTLGRRLACL FLACVLPALL LGGTALASER GLWEKGYTGA KVKMAIFDTG IRANHPHFRN<br>61 IKERTNWTNE DTLNDNLGHG TFVAGVIAGQ YDECLGFAPD TEIYAFRVFT DAQVSYTSWF<br>121 LDAFNYAIAT NMDVLNLSIG GPDYLDLPFV EKVWELTANN IIMVSAIGND GPLYGTLNNP<br>181 ADQSDVIGVI DYGDHIASFS SRGMSTWEIP HGYGRVKPDV VAYGREIMGS SISANCKSLS<br>241 GTSVASPVVA GVVCLLVSVI PEHDRKNILN PASMKQALVE GAARLPDANM YEQGAGR |

Table legend: For chimeric peptide sequences, italics indicates BPI/LBP or subtilisin/ subtilisin; bold indicates Linker; italics underline bold indicates Thionin and underline indicates Signal sequence.

The chimera protein of an embodiment of the present invention may be produced using any of a number of systems to obtain the desired quantities of the protein. There are many expression systems well known in the art. (See, e.g., Gene Expression Systems, Fernandes and Hoeffler, Eds. Academic Press, 1999; Ausubel, supra.) Typically, the polynucleotide that encodes the chimera or component thereof is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs". Accordingly, the nucleic acids that encode the joined polypeptides are incorporated for high level expression in a desired host cell.

The production of CHAMPs as secreted proteins in plant, insect and mammalian expression systems is generally preferred, since the active components of the chimera will typically require various post-translational modifications to produce correctly-folded, biologically active polypeptides. In particular, given that defensins contain up to four disulfide bridges that are required for functional activity, and SRDs may contain glycosylation sites and disulfide bonds, expression of SRD/defensin chimeras as secreted proteins is preferred in order to take advantage of the robust structural integrity rendered by these post-translational modifications.

For example, insect cells possess a compartmentalized secretory pathway in which newly synthesized proteins that bear an N-terminal signal sequence transit from the endoplasmic reticulum (ER), to the Golgi apparatus, and finally to the cell surface via vesicular intermediates. The compartments of the secretory pathway contain specialized environments that enhance the ability of proteins that pass through to fold correctly and assume a stable conformation. For example, the ER supports an oxidizing environment that catalyzes disulfide bond formation, and both the ER and Golgi apparatus contains glycosylation enzymes that link oligosaccharide chains to secretory proteins to impart stability and solubility. In general, secreted proteins receive these modifications as a way of stabilizing protein structure in the harsher environment of the cell surface, in the presence of extracellular proteases and pH changes. One example of an insect expression system that may be used to express the chimeras of the invention is a Bacculovirus expression system (see below). The use of a Bacculovirus expression system to express a prototype SRD/defensin chimera is illustrated in Example 3, infra.

To illustrate, chimeras may be expressed in a Baculovirus system as follows. Briefly, DNA expressing a chimera are cloned into a modified form of the Baculovirus transfer vector pAcGP67B (Pharmingen, San Diego, Calif.). This plasmid contains the signal sequence for gp67, an abundant envelope surface glycoprotein on *Autographa californica* nuclear polyhedrosis virus (AcNPV) that is essential for the entry of Baculovirus particles into target insect cells. Insertion of the chimera gene into this vector will yield expression of a gp67 signal peptide fusion to the chimera, under the control of the strong Baculovirus polyhedrin promoter. The signal peptide will direct the entire protein through the secretory pathway to the cell surface, where the signal peptide is cleaved off and the chimera protein can be purified from the cell supernatant.

The Baculovirus transfer vector pAcGP67B may be modified by inserting a myc epitope and 6.times.His tag at the 3' end of the multiple cloning region for identification and purification purposes (pAcGP67B-MH). Chimera genes inserted into pAcGP67B-MH may be co-transfected with Baculogold DNA into Sf21 cells using the Baculogold transfection kit (Pharmingen). Recombinant viruses formed by homologous recombination are amplified, and the protein purified from a final amplification in High Five cells (Invitrogen, Carlsbad, Calif.), derived from *Trichoplusia ni* egg cell homogenates. High Five cells have been shown to be capable of expressing significantly higher levels of secreted recombinant proteins compared to Sf9 and Sf21 insect cells.

Various transgenic plant expression systems may also be utilized for the generation of the chimera proteins of the invention, including without limitation tobacco and potato plant systems (e.g., see Mason et al., 1996, Proc. Natl. Acad. Sci. USA 93: 5335-5340).

Optionally, a bioreactor may be employed, such as the CELLine 350 bioreactor (Integra Biosciences). This particular bioreactor provides for culturing the plant cells within a relatively low-volume, rectangular chamber (5 ml), bounded by an oxygen-permeable membrane on one side, and a protein-impermeable, 10 kD molecular weight cut-off membrane on the other side, separating the cell compartment from the larger (350 ml) nutrient medium reservoir. The use of such a bioreactor permits simple monitoring of protein concentrations in the cell chamber, as a function of time, and simple characterization of proteins secreted into the medium using SDS-PAGE. Thus, such bioreactors also facilitate the expression of heterologous proteins in plant expression systems. Various other bioreactor and suspension-culture systems may be employed. See, for example, Decendit et al., 1996, Biotechnol. Lett. 18: 659-662.

Generation of Xf Resistant Transgenic Plants:

Genes encoding the anti-Xf chimeras of the invention may be introduced into grapevines using several types of transformation approaches developed for the generation of transgenic plants (see, for example, Szankowski et al., 2003 Plant Cell Rep. 22: 141-149). Standard transformation techniques, such as *Agrobacterium*-mediated transformation, particle bombardment, microinjection, and electroporation may be utilized to construct stably-transformed transgenic plants (Hiatt et al., 1989, Nature 342: 76-78). In addition, recombinant viruses which infect grapevine plants may be used to express the heterologous chimera protein of interest during viral replication in the infected host (see, for example, Kumagai et al., 1993, Proc. Natl. Acad. Sci. USA 90: 427-430).

Vectors capable of facilitating the expression of a transgene in embryogenic cells of grapevine plants are known, several of which are shown in FIG. 9 by way of illustration, not limitation (see, for example, Verch et al., 2004. Cancer Immunol. Immunother. 53: 92-99; Verch et al., 1998. J. Immunol. Methods 220: 69-75; Mason et al., 1996, Proc. Natl. Acad. Sci. USA 93: 5335-5340). See, also, Szankowski et al., 2003, Plant Cell Rep. 22: 141-149.

As shown by the results of the study described in Example 4, supra, transgenic grape plants expressing a test protein in the plant's xylem can be generated using standard methodologies. In one embodiment, the genetic information necessary to express an anti-Xf chimera may be introduced into grapevine embryonic cells to generate transgenic grapevines expressing the chimera using standard transgenic methodologies. In preferred embodiments, DNA encoding the chimera is fused to a xylem targeting sequence or a secretion leader peptide from a xylem-expressed plant protein or precursor. In view of the success achieved with the test protein, pear PGIP (see Example 4, supra), a specific embodiment utilizes the PGIP secretion leader peptide:

(SEQ ID NO. 26)
MELKFSTFLSLTLLFSSVLNPALS.

Another example of a secretion leader which may be employed is the rice alpha-amylase leader:

(SEQ ID NO. 25)
MGKHHVTLCCVVFAVLCLASSLAQA.

As is known in the art, different organisms preferentially utilize different codons for generating polypeptides. Such "codon usage" preferences may be used in the design of nucleic acid molecules encoding the chimeras of the invention in order to optimize expression in a particular host cell system.

Another embodiment provides for treating infected plants with topical chimera protein as described herein. The signal sequence at the N-terminus will not be present in the protein chimera for topical use. Topical treatment will clear Xf from infected plants according to one embodiment. The ability to produce the chimeras on a large scale will also allow topical delivery to cure grapevines already infected with Xf and block PD. We also have the ability to further improve the activity of (BPI/LBP and defensin) and (subtilisin and defensin) chimeras.

Treatment of Pierce's Disease:

The anti-*Xylella fastidiosa* chimeras of the invention may be used for the treatment of Pierce's Disease in grapevines. Candidate chimeras may be initially evaluated using cell survival assays capable of assessing Xf killing. Chimeras showing activity in such in vitro assay systems may be further evaluated in plant assay systems. Chimeras demonstrating Xf killing in these systems may be used for the therapeutic treatment of symptomatic or asymptomatic grapevines or for the prophylactic treatment of vines exposed to Xf or at risk of being exposed to Xf.

For therapeutic treatment, an anti-pathogen chimera (for example an anti-Xf chimera) is administered to the affected plant in a manner that permits the chimera to gain access to the xylem, where Xf colonies are located. Accordingly, the chimera may be administered directly to the xylem system, for example, via microinjection into the plant (e.g., stem, petiole, trunk). In one embodiment, anti-Xf chimera composition is injected directly into an infected grapevine, in one embodiment via a plugged, approximately 0.5 cm hole drilled into the vine, through which a syringe containing the composition may be inserted to deliver the composition to the xylem.

In one embodiment, a method of treating Pierce's Disease in a Vitus *vinifera* plant infected with Xf, comprises spraying the Vitus *vinifera* plant with an adherent composition containing an anti-Xf chimera. Various adherent compositions are known, and typically are formulated in liquid for ease of application with a sprayer. Adherent powders or semi-liquids may also be employed. A related embodiment is a method of preventing the development of Pierce's Disease in a Vitus *vinifera* plant, and comprises spraying the Vitus *vinifera* plant with an adherent composition containing an anti-Xf chimera.

Alternatively, an expressible gene encoding the chimera may be introduced into a plant virus capable of infecting grapevine plants, and the recombinant virus used to infect the plant, resulting in the expression of the chimera in the plant. In such applications, the use of xylem secretory signals may be used to target the chimera product to the infected plant's xylem.

The chimera may also be administered to the plant via the root system, in order to achieve systemic administration and access to primary xylem chambers. Similarly, the chimera may be administered to vine trunks, directly into primary xylem chambers, in order to deliver the chimera to upstream xylem throughout the plant.

The treatment of Pierce's Disease using the chimeras of the invention may also target the insect vectors responsible for the spread of Pierce's Disease. In this aspect of the invention, anti-Xf chimeras are introduced into the insect vector itself, so that the chimera can kill the Xf colonies residing in the insect, thereby inhibiting the further spread of the pathogen. In one embodiment, plants susceptible to feeding by a Xf vector insect (e.g., glassy winged sharpshooter) are sprayed with a composition that comprises the chimera and a carrier capable of adhering to the surface of the vine plants. When the vector insect feeds upon the treated plant, some of the composition is both ingested by the insect and injected into the plant. In effect, the insect thereby mediates the injection of the composition into the plant's xylem sap as it feeds on the plant. Accordingly, the anti-microbial composition then has the opportunity to inhibit the development of Xf colonies in the newly infected plant by killing bacteria at the feeding insertion site. Additionally, the ingestion of the composition by the insect also provides an opportunity to target and kill Xf colonies residing inside the vector insect, thereby inhibiting further spread.

Variations of this approach are contemplated. For example, a composition comprising an anti-Xf chimera of an embodiment of the present invention, an insect food source, and/or a biological or chemical insect attractant may be placed locally in regions at risk for, or known to be susceptible to, insect-vectored Xf (e.g., vineyards, groves). In one embodiment, such a composition comprises an anti-Xf chimera solubilized in a sucrose solution. In another embodiment, the anti-Xf composition may be solubilized or suspended in a sap or sap-containing solution, preferably using sap from the insect vector's natural food sources. The composition may be exposed to the insect vector in any number of ways, including for example by placing appropriate feeder vessels in susceptible vineyards, adjacent crop areas, inhabited groves or in breeding habitats. In this regard, the glassy-winged sharpshooter inhabits citrus and avocado groves and some woody ornamentals in unusually high numbers. At immediate risk are vineyards near citrus orchards.

In addition to the treatment of established Xf infections, diseases caused by Xf may be prevented or inhibited using the chimeras of the invention in a prophylactic treatment approach, using the same or similar methods as described above. In one approach, for example, plants which are not susceptible to Xf infection and/or Xf-caused disease, but which are used by Xf insect vectors to breed or feed, may be sprayed with a composition containing an anti-Xf chimera of the invention. Insect vectors feeding upon such plants, for example, will ingest the composition, which is then available to kill Xf present in the insect vector, thereby preventing the spread of new infections to susceptible or carrier plants.

Example 1

Human proteinase K is very well characterized and the cleavage analysis shows that it is more active on Xf mopB than HNE. Proteainase K homologs in grape belong to subtilisin family and they have 43% sequence similarity to human proteinase *K*. *Subtilisin*-like protease SBT6.1 from *Vitis vinifera* with the sequence shown in FIG. 4. Among grape defensins, the gamma thionin family members appear to be more effective on gram-negative bacteria such as Xf. We have chosen a member of the gamma thionin family as the lysis element/domain for our chimera. We have also added another thionin version with VFDEK (SEQ ID NO. 29) added at the C terminal to increase activity and lower toxicity. The human BPI/LBP protein has been shown to have activities on the outer-membrane of gram-negative bacteria. The members of grape BPI/LBP family members have similar domain structures as the human homolog and show 43% sequence similarity. Initially, we have chosen one member of the grape BPI/LBP family for our chimera. Several types of linkers are chosen: for example, a synthetic GSTAPPA (SEQ ID NO: 18) linker and another a natural linker, RANATTLPKYYQNSRHPVSCTDPSK (SEQ ID NO: 19), that joins the two similar domains of BPI/LBP. Structure-based method previously developed by us was employed to design the chimera using recognition domain, linker, and lysis domain. The designed protein chimeras will be expressed in eukaryotic systems by the methods developed by us. The expressed and purified protein chimeras will be tested for their in vitro activities. Finally, transgenic grapes will be generated using *Agrobacterium* mediated transformation or precision breeding by CRISPR/CAS.

The preceding examples can be repeated with similar success by substituting the generically or specifically described reactants and/or operating conditions of this invention for those used in the preceding examples.

Although the invention has been described in detail with particular reference to examples, and one or more embodiments, other embodiments can achieve the same results. Identity can be calculated by known methods. Identity, or homology, percentages as mentioned herein are those that can be calculated with the Blast or GAP program, running under GCG (Genetics Computer Group Inc., Madison, Wis., USA). Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Nat. Acad Sci. USA 85:2444, 1988; Higgins & Sharp, Gene, 73:23744, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth Mol. Bio. 24:307-31, 1994. Altschul et al., J. Mol. Biol. 215:403-10, 1990, presents a detailed consideration of sequence alignment methods and homology calculations. A chimera protein of the disclosure can have about 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to at least one of the SEQ ID Nos 4-7 and 30-33. A sequence that forms part of the chimera protein of the disclosure can have 5%, about 10%, about 15%, about 20%, about 25%, about 30%, about 35%, about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% amino acid sequence homology to a subtilisin, BPI/LBP or definsin amino acid sequence as disclosed herein. A chimera protein expressed in the host can be mature and not include the signal sequence.

Variations and modifications of the present invention will be obvious to those skilled in the art and it is intended to cover in the appended claims all such modifications and equivalents. The entire disclosures of all references, applications, patents, and publications cited above are hereby incorporated by reference.

LITERATURE CITED

*Paradigms: examples from the bacterium Xylella fastidiosa.* Purcell A. Annu Rev Phytopathol. 2013; 51:339-56. doi: 10.1146/annurev-phyto-082712-102325.

*The biology of xylem fluid-feeding insect vectors of Xylella fastidiosa and their relation to disease epidemiology.* Redak R A, Purcell A H, Lopes J R, Blua M J, Mizell R F 3rd, Andersen P C. Annu Rev Entomol. 2004; 49:243-70.

Pierce's Disease, Special Notices, Pierce's Disease Brochure: A Decade of Progress, 2009, http://www.wineinstitute.org/initiatives/issuesandpolicy/piercesdisease The Costs of Pierce's Disease in the California Winegrape Industry, Kabir P. Tumber, Julian M. Alston, and Kate B. Fuller, 2012, CWE Working Paper number 1204, published by Robert Mandavi Institute, Center for Wine Economics; see also http://californiaagriculture.ucanr.edu/landingpage.cfm?article=ca.v068n01p20&fulltext=yes, Pierce's disease costs California $104 million per year by Kabir P. Tumber, Julian M. Alston and Kate B. Fuller Economic Consequences of Pierce's Disease and Related Policy in the California Wine grape Industry, Julian M. Alston, Kate B. Fuller, Jonathan D. Kaplan. and Kabir P. Tumber, Journal of Agricultural and Resource Economics 38(2):269-297.

*An engineered innate immune defense protects grapevines from Pierce disease.* Dandekar A M, Gouran H, Ibifez A M, Uratsu S L, Agilero C B, McFarland S, Borhani Y, Feldstein P A, Bruening G, Nascimento R, Goulart L R, Pardington P E, Chaudhary A, Norvell M, Civerolo E, Gupta G. Proc Natl Acad Sci USA. 2012 Mar. 6; 109(10): 3721-5.

*Degradation of outer membrane protein A in Escherichia coli killing by neutrophil elastase.* Belaaouaj A, Kim K S, Shapiro S D. Science. 2000 Aug. 18; 289(5482):1185-8.

Broad activity against porcine bacterial pathogens displayed by two insect antimicrobial peptides moricin and cecropin B. Hu H, Wang C, Guo X, Li W, Wang Y, He Q. Mol Cells. 2013 February; 35(2):106-14.

Galvez, L. C., Korus, K., Fernandez, J., Behn, J. L., and Banjara, N. 2010. The Threat of Pierce's Disease to Midwest Wine and Table Grapes. Online. APSnet Features. doi:10.1094/APSnetFeature-2010-1015.

Natural hosts of *Xylella fastidiosa* in Florida. Hopkins D. L., Adlerz W. C., 1988. *Plant Disease* 72: 429-431.

*Identification and characterization of the defensin-like gene family of grapevine.* Giacomelli L, Nanni V. Lenzi L, Zhuang J, Dalla Serra M Banfield M J, Town C D, Silverstein K A, Baraldi E, Moser C. Mol Plant Microbe Interact. 2012 August; 25(8):1118-31.

*Proteinase K and the structure of PrPSc: The good, the bad and the ugly.* Silva C J, Vizquez-Fernández E, Onisko B. Requena J R. Virus Res. 2015 Sep. 2; 207:120-6.

*The BPI/LBP family of proteins: a structural analysis of conserved regions.* Beamer L J, Carroll S F, Eisenberg D. Protein Sci. 1998 April; 7(4):906-14. Look up https://www.ncbi.nlm.nih.gov/protein/XP_002277143.2 for the grape homolog.

Genome-wide and molecular evolution analysis of the subtilase gene family in *Vitis vinifera*. Cao J, Han X, Zhang T, Yang Y, Huang J, Hu X. BMC Genomics. 2014 Dec. 16; 15:1116

*Suitability of non-lethal marker and marker-free systems for development of transgenic crop plants: present status and future prospects.* Manimaran P, Ramkumar G, Sakthivel K, Sundaram R M, Madhav M S, Balachandran S M. Biotechnol Adv. 2011 November-December; 29(6):703-14.

*Identification of genomic sites for CRISPR/Cas9-based genome editing in the Vitis vinifera genome.* Wang Y, Liu X, Ren C, Zhong G Y, Yang L, Li S, Liang Z. BMC Plant Biol. 2016 Apr. 21; 16:96.

expasy.org/tools/peptidecutter PeptideCutter [references/documentation] predicts potential cleavage sites cleaved by proteases or chemicals in a given protein sequence.

*Plant gamma-thionins: novel insights on the mechanism of action of a multi-functional class of defense proteins.* Pelegrini P B, Franco O L. Int J Biochem Cell Biol. 2005 November; 37(11):2239-53.

*Rapid clearance of bacteria and their toxins: development of therapeutic proteins.* Kunkel M, Vuyisich M, Gnanakaran G, Bruening G E, Dandekar A M, Civerolo E, Marchalonis J J, Gupta G. Crit Rev Immunol. 2007; 27(3):233-45.

*A dual-purpose protein ligand for effective therapy and sensitive diagnosis of anthrax.* Vuyisich M, Gnanakaran S. Lovchik J A, Lyons C R, Gupta G. Protein J. 2008 August; 27(5):292-302

What is claimed is:

1. A chimeric protein comprising an amino acid sequence selected from the group consisting of SEQ ID NO: 4, 5, 6, 7, 30, 31, 32, and 33.

2. A nucleic acid sequence encoding the chimeric protein of claim 1.

3. An expression vector comprising the nucleic acid sequence of claim 2 and an operably linked promoter.

4. A genetically altered plant or seed, comprising the nucleic acid sequence of claim 2 operably linked to a promoter such that the genetically altered plant or a plant that grows from the seed produces the chimeric protein.

5. A plant cell comprising the nucleic acid sequence of claim 2 operably linked to a promoter such that the plant cell produces the chimeric protein.

6. A tissue culture comprising the plant cell of claim 5.

7. An expression vector for *agrobacterium*-mediated transformation using the polynucleotide in claim 2.

8. A method of treating a plant at risk for infection with *Xylella fastidiosa* (Xf), comprising:
    applying the chimeric protein of claim 1 to the plant at risk of infection with Xf.

9. A method of treating a production crop plant that is at risk for becoming infected with a pathogen that will harm the production crop plant, comprising:
    applying topically a chimeric protein of claim 1 to the production crop plant at risk of becoming infected.

10. A method of treating a production crop plant that is at risk for becoming infected with a pathogen that will harm the production crop plant, comprising:
    transforming the production crop with a nucleic acid sequence that encodes a chimeric protein of claim 1.

11. The method of claim 10, wherein transforming the production crop comprises transforming a scion cultivar or root stock cultivar.

12. A method of conferring resistance against a disease to a production crop scion cultivar or a production crop rootstock cultivar, comprising:
    transforming a production crop scion cultivar or production crop rootstock cultivar with a nucleic acid sequence that encodes the chimeric protein of claim 1.

13. A transgenic production crop scion cultivar or transgenic production crop rootstock cultivar transformed with a polynucleotide comprising a nucleic acid sequence that encodes for a chimeric protein of claim 1.

* * * * *

SEQUENCE LISTING

<160> NUMBER OF SEQ ID NOS: 36

<210> SEQ ID NO 1
<211> LENGTH: 297
<212> TYPE: PRT
<213> ORGANISM: Artificial Sequence
<220> FEATURE:

<223> OTHER INFORMATION: synthetic construct
<220> FEATURE:
<221> NAME/KEY: MISC_FEATURE
<223> OTHER INFORMATION: synthetic construct

<400> SEQUENCE: 1

```
Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Arg Gly Leu
            20                  25                  30

Trp Glu Lys Gly Tyr Thr Gly Ala Lys Val Lys Met Ala Ile Phe Asp
        35                  40                  45

Thr Gly Ile Arg Ala Asn His Pro His Phe Arg Asn Ile Lys Glu Arg
    50                  55                  60

Thr Asn Trp Thr Asn Glu Asp Thr Leu Asn Asp Asn Leu Gly His Gly
65                  70                  75                  80

Thr Phe Val Ala Gly Val Ile Ala Gly Gln Tyr Asp Glu Cys Leu Gly
                85                  90                  95

Phe Ala Pro Asp Thr Glu Ile Tyr Ala Phe Arg Val Phe Thr Asp Ala
            100                 105                 110

Gln Val Ser Tyr Thr Ser Trp Phe Leu Asp Ala Phe Asn Tyr Ala Ile
        115                 120                 125

Ala Thr Asn Met Asp Val Leu Asn Leu Ser Ile Gly Gly Pro Asp Tyr
    130                 135                 140

Leu Asp Leu Pro Phe Val Glu Lys Val Trp Glu Leu Thr Ala Asn Asn
145                 150                 155                 160

Ile Ile Met Val Ser Ala Ile Gly Asn Asp Gly Pro Leu Tyr Gly Thr
                165                 170                 175

Leu Asn Asn Pro Ala Asp Gln Ser Asp Val Ile Gly Val Ile Asp Tyr
            180                 185                 190

Gly Asp His Ile Ala Ser Phe Ser Ser Arg Gly Met Ser Thr Trp Glu
        195                 200                 205

Ile Pro His Gly Tyr Gly Arg Val Lys Pro Asp Val Val Ala Tyr Gly
    210                 215                 220

Arg Glu Ile Met Gly Ser Ser Ile Ser Ala Asn Cys Lys Ser Leu Ser
225                 230                 235                 240

Gly Thr Ser Val Ala Ser Pro Val Val Ala Gly Val Val Cys Leu Leu
                245                 250                 255

Val Ser Val Ile Pro Glu His Asp Arg Lys Asn Ile Leu Asn Pro Ala
            260                 265                 270

Ser Met Lys Gln Ala Leu Val Glu Gly Ala Ala Arg Leu Pro Asp Ala
        275                 280                 285

Asn Met Tyr Glu Gln Gly Ala Gly Arg
    290                 295
```

<210> SEQ ID NO 2
<211> LENGTH: 79
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthetic construct

<400> SEQUENCE: 2

```
Met Glu Arg Lys Ser Leu Gly Phe Phe Phe Leu Leu Leu Ile Leu
1               5                   10                  15
```

```
Leu Ala Ser Gln Met Val Pro Ser Glu Ala Arg Val Cys Glu Ser
            20                  25                  30

Gln Ser His Lys Phe Glu Gly Ala Cys Met Gly Asp His Asn Cys Ala
        35                  40                  45

Leu Val Cys Arg Asn Gly Phe Ser Gly Lys Cys Lys Gly Leu
    50                  55                  60

Arg Arg Arg Cys Phe Cys Thr Lys Leu Cys Val Phe Asp Glu Lys
65                  70                  75
```

<210> SEQ ID NO 3
<211> LENGTH: 280
<212> TYPE: PRT
<213> ORGANISM: Artificial Sequence
<220> FEATURE:
<223> OTHER INFORMATION: synthetic construct

<400> SEQUENCE: 3

```
Met Arg Pro Ser Val Leu Val Ile Phe Ile Ala Phe Leu Leu Phe Thr
1               5                   10                  15

Pro Ser Gln Ala His Leu Lys Ser Thr Glu Ser Ser Phe Ile Ser Ile
            20                  25                  30

Leu Ile Ser Ser Gln Gly Leu Asp Phe Ile Lys Asn Leu Leu Ile Thr
        35                  40                  45

Lys Ala Ile Ser Ser Leu Thr Pro Leu Gln Leu Pro Gln Ile Lys Lys
    50                  55                  60

Ser Val Lys Ile Pro Phe Leu Gly Arg Val Asp Ile Ala Phe Ser Asn
65                  70                  75                  80

Ile Thr Ile Tyr His Ile Asp Val Ser Ser Asn Ile Ala Pro Gly
                85                  90                  95

Asp Thr Gly Val Ala Ile Ile Ala Ser Gly Thr Thr Cys Asn Leu Ser
            100                 105                 110

Met Asn Trp His Tyr Ser Tyr Asn Thr Trp Phe Val Pro Val Glu Ile
        115                 120                 125

Ser Asp Ser Gly Thr Ala Gln Val Gln Val Glu Gly Met Glu Val Gly
    130                 135                 140

Leu Thr Leu Gly Leu Glu Asn Arg Glu Gly Ser Met Lys Leu Ser Ala
145                 150                 155                 160

Lys Asp Cys Gly Cys Tyr Val Glu Asp Ile Ser Ile Lys Leu Asp Gly
                165                 170                 175

Gly Ala Ser Trp Leu Tyr Gln Gly Val Val Asp Ala Phe Glu Glu Gln
            180                 185                 190

Ile Gly Ser Ala Val Glu Ser Thr Ile Thr Lys Lys Leu Lys Glu Gly
        195                 200                 205

Ile Ile Lys Leu Asp Ser Phe Leu Gln Ala Leu Pro Lys Glu Ile Pro
    210                 215                 220

Val Asp Asn Ile Ala Ser Leu Asn Val Thr Phe Val Asn Asp Pro Leu
225                 230                 235                 240

Leu Ser Asn Ser Ser Ile Gly Phe Asp Ile Asn Gly Leu Phe Thr Arg
                245                 250                 255

Ala Asn Ala Thr Thr Leu Pro Lys Tyr Tyr Gln Asn Ser Arg His Pro
            260                 265                 270

Val Ser Cys Thr Asp Pro Ser Lys
        275                 280
```

<210> SEQ ID NO 4

<211> LENGTH: 307
<212> TYPE: PRT
<213> ORGANISM: Artificial Sequence
<220> FEATURE:
<223> OTHER INFORMATION: synthetic construct

<400> SEQUENCE: 4

```
Met Glu Arg Lys Ser Leu Gly Phe Phe Phe Leu Leu Leu Ile Leu
1               5                   10                  15

Leu Ala Ser Gln Met Val Val Pro Ser Glu Ala Arg Val Cys Glu Ser
            20                  25                  30

Gln Ser His Lys Phe Glu Gly Ala Cys Met Gly Asp His Asn Cys Ala
                35                  40                  45

Leu Val Cys Arg Asn Glu Gly Phe Ser Gly Gly Lys Cys Lys Gly Leu
    50                  55                  60

Arg Arg Arg Cys Phe Cys Thr Lys Leu Cys Val Phe Asp Glu Lys Gly
65                  70                  75                  80

Ser Thr Ala Pro Pro Ala Ser Ser Gln Gly Leu Asp Phe Ile Lys Asn
                85                  90                  95

Leu Leu Ile Thr Lys Ala Ile Ser Ser Leu Thr Pro Leu Gln Leu Pro
                100                 105                 110

Gln Ile Lys Lys Ser Val Lys Ile Pro Phe Leu Gly Arg Val Asp Ile
            115                 120                 125

Ala Phe Ser Asn Ile Thr Ile Tyr His Ile Asp Val Ser Ser Ser Asn
    130                 135                 140

Ile Ala Pro Gly Asp Thr Gly Val Ala Ile Ile Ala Ser Gly Thr Thr
145                 150                 155                 160

Cys Asn Leu Ser Met Asn Trp His Tyr Ser Tyr Asn Thr Trp Phe Val
                165                 170                 175

Pro Val Glu Ile Ser Asp Ser Gly Thr Ala Gln Val Gln Val Glu Gly
            180                 185                 190

Met Glu Val Gly Leu Thr Leu Gly Leu Glu Asn Arg Glu Gly Ser Met
        195                 200                 205

Lys Leu Ser Ala Lys Asp Cys Gly Cys Tyr Val Glu Asp Ile Ser Ile
    210                 215                 220

Lys Leu Asp Gly Gly Ala Ser Trp Leu Tyr Gln Gly Val Val Asp Ala
225                 230                 235                 240

Phe Glu Glu Gln Ile Gly Ser Ala Val Glu Ser Thr Ile Thr Lys Lys
                245                 250                 255

Leu Lys Glu Gly Ile Ile Lys Leu Asp Ser Phe Leu Gln Ala Leu Pro
            260                 265                 270

Lys Glu Ile Pro Val Asp Asn Ile Ala Ser Leu Asn Val Thr Phe Val
        275                 280                 285

Asn Asp Pro Leu Leu Ser Asn Ser Ser Ile Gly Phe Asp Ile Asn Gly
    290                 295                 300

Leu Phe Thr
305
```

<210> SEQ ID NO 5
<211> LENGTH: 332
<212> TYPE: PRT
<213> ORGANISM: Artificial Sequence
<220> FEATURE:
<223> OTHER INFORMATION: synthetic construct

<400> SEQUENCE: 5

Met Arg Pro Ser Val Leu Val Ile Phe Ile Ala Phe Leu Leu Phe Thr

```
            1               5              10              15
        Pro Ser Gln Ala His Leu Lys Ser Thr Glu Ser Ser Phe Ile Ser Ile
                        20              25              30

Leu Ile Ser Ser Gln Gly Leu Asp Phe Ile Lys Asn Leu Leu Ile Thr
                        35              40              45

Lys Ala Ile Ser Ser Leu Thr Pro Leu Gln Leu Pro Gln Ile Lys Lys
                    50              55              60

Ser Val Lys Ile Pro Phe Leu Gly Arg Val Asp Ile Ala Phe Ser Asn
         65              70              75              80

Ile Thr Ile Tyr His Ile Asp Val Ser Ser Asn Ile Ala Pro Gly
                            85              90              95

Asp Thr Gly Val Ala Ile Ile Ala Ser Gly Thr Thr Cys Asn Leu Ser
                            100             105             110

Met Asn Trp His Tyr Ser Tyr Asn Thr Trp Phe Val Pro Val Glu Ile
                            115             120             125

Ser Asp Ser Gly Thr Ala Gln Val Gln Val Glu Gly Met Glu Val Gly
                    130             135             140

Leu Thr Leu Gly Leu Glu Asn Arg Glu Gly Ser Met Lys Leu Ser Ala
        145             150             155             160

Lys Asp Cys Gly Cys Tyr Val Glu Asp Ile Ser Ile Lys Leu Asp Gly
                        165             170             175

Gly Ala Ser Trp Leu Tyr Gln Gly Val Val Asp Ala Phe Glu Glu Gln
                        180             185             190

Ile Gly Ser Ala Val Glu Ser Thr Ile Thr Lys Lys Leu Lys Glu Gly
                        195             200             205

Ile Ile Lys Leu Asp Ser Phe Leu Gln Ala Leu Pro Lys Glu Ile Pro
                        210             215             220

Val Asp Asn Ile Ala Ser Leu Asn Val Thr Phe Val Asn Asp Pro Leu
        225             230             235             240

Leu Ser Asn Ser Ser Ile Gly Phe Asp Ile Asn Gly Leu Phe Thr Arg
                        245             250             255

Ala Asn Ala Thr Thr Leu Pro Lys Tyr Tyr Gln Asn Ser Arg His Pro
                        260             265             270

Val Ser Cys Thr Asp Pro Ser Lys Arg Val Cys Glu Ser Gln Ser His
                        275             280             285

Lys Phe Glu Gly Ala Cys Met Gly Asp His Asn Cys Ala Leu Val Cys
                        290             295             300

Arg Asn Glu Gly Phe Ser Gly Gly Lys Cys Lys Gly Leu Arg Arg Arg
        305             310             315             320

Cys Phe Cys Thr Lys Leu Cys Val Phe Asp Glu Lys
                        325             330
```

<210> SEQ ID NO 6
<211> LENGTH: 354
<212> TYPE: PRT
<213> ORGANISM: Artificial Sequence
<220> FEATURE:
<223> OTHER INFORMATION: synthetic construct

<400> SEQUENCE: 6

```
Met Glu Arg Lys Ser Leu Gly Phe Phe Phe Leu Leu Leu Ile Leu
1               5                   10                  15

Leu Ala Ser Gln Met Val Val Pro Ser Glu Ala Arg Val Cys Glu Ser
                20              25              30

Gln Ser His Lys Phe Glu Gly Ala Cys Met Gly Asp His Asn Cys Ala
```

```
            35                  40                  45
Leu Val Cys Arg Asn Glu Gly Phe Ser Gly Gly Lys Cys Lys Gly Leu
 50                  55                  60

Arg Arg Arg Cys Phe Cys Thr Lys Leu Cys Val Phe Asp Glu Lys Gly
 65                  70                  75                  80

Ser Thr Ala Pro Pro Ala Arg Gly Leu Trp Glu Lys Gly Tyr Thr Gly
                 85                  90                  95

Ala Lys Val Lys Met Ala Ile Phe Asp Thr Gly Ile Arg Ala Asn His
            100                 105                 110

Pro His Phe Arg Asn Ile Lys Glu Arg Thr Asn Trp Thr Asn Glu Asp
        115                 120                 125

Thr Leu Asn Asp Asn Leu Gly His Gly Thr Phe Val Ala Gly Val Ile
    130                 135                 140

Ala Gly Gln Tyr Asp Glu Cys Leu Gly Phe Ala Pro Asp Thr Glu Ile
145                 150                 155                 160

Tyr Ala Phe Arg Val Phe Thr Asp Ala Gln Val Ser Tyr Thr Ser Trp
                165                 170                 175

Phe Leu Asp Ala Phe Asn Tyr Ala Ile Ala Thr Asn Met Asp Val Leu
            180                 185                 190

Asn Leu Ser Ile Gly Gly Pro Asp Tyr Leu Asp Leu Pro Phe Val Glu
        195                 200                 205

Lys Val Trp Glu Leu Thr Ala Asn Asn Ile Ile Met Val Ser Ala Ile
    210                 215                 220

Gly Asn Asp Gly Pro Leu Tyr Gly Thr Leu Asn Asn Pro Ala Asp Gln
225                 230                 235                 240

Ser Asp Val Ile Gly Val Ile Asp Tyr Gly Asp His Ile Ala Ser Phe
                245                 250                 255

Ser Ser Arg Gly Met Ser Thr Trp Glu Ile Pro His Gly Tyr Gly Arg
            260                 265                 270

Val Lys Pro Asp Val Val Ala Tyr Gly Arg Glu Ile Met Gly Ser Ser
        275                 280                 285

Ile Ser Ala Asn Cys Lys Ser Leu Ser Gly Thr Ser Val Ala Ser Pro
    290                 295                 300

Val Val Ala Gly Val Val Cys Leu Leu Val Ser Val Ile Pro Glu His
305                 310                 315                 320

Asp Arg Lys Asn Ile Leu Asn Pro Ala Ser Met Lys Gln Ala Leu Val
                325                 330                 335

Glu Gly Ala Ala Arg Leu Pro Asp Ala Asn Met Tyr Glu Gln Gly Ala
            340                 345                 350

Gly Arg

<210> SEQ ID NO 7
<211> LENGTH: 356
<212> TYPE: PRT
<213> ORGANISM: Artificial Sequence
<220> FEATURE:
<223> OTHER INFORMATION: synthetic construct

<400> SEQUENCE: 7

Met Thr Leu Gly Arg Arg Leu Ala Cys Leu Phe Leu Ala Cys Val Leu
 1               5                  10                  15

Pro Ala Leu Leu Leu Gly Gly Thr Ala Leu Ala Ser Glu Arg Gly Leu
                20                  25                  30

Trp Glu Lys Gly Tyr Thr Gly Ala Lys Val Lys Met Ala Ile Phe Asp
            35                  40                  45
```

```
Thr Gly Ile Arg Ala Asn His Pro His Phe Arg Asn Ile Lys Glu Arg
         50                  55                  60

Thr Asn Trp Thr Asn Glu Asp Thr Leu Asn Asp Asn Leu Gly His Gly
 65                  70                  75                  80

Thr Phe Val Ala Gly Val Ile Ala Gly Gln Tyr Asp Glu Cys Leu Gly
                 85                  90                  95

Phe Ala Pro Asp Thr Glu Ile Tyr Ala Phe Arg Val Phe Thr Asp Ala
                100                 105                 110

Gln Val Ser Tyr Thr Ser Trp Phe Leu Asp Ala Phe Asn Tyr Ala Ile
            115                 120                 125

Ala Thr Asn Met Asp Val Leu Asn Leu Ser Ile Gly Gly Pro Asp Tyr
        130                 135                 140

Leu Asp Leu Pro Phe Val Glu Lys Val Trp Glu Leu Thr Ala Asn Asn
145                 150                 155                 160

Ile Ile Met Val Ser Ala Ile Gly Asn Asp Gly Pro Leu Tyr Gly Thr
                165                 170                 175

Leu Asn Asn Pro Ala Asp Gln Ser Asp Val Ile Gly Val Ile Asp Tyr
                180                 185                 190

Gly Asp His Ile Ala Ser Phe Ser Ser Arg Gly Met Ser Thr Trp Glu
            195                 200                 205

Ile Pro His Gly Tyr Gly Arg Val Lys Pro Asp Val Val Ala Tyr Gly
        210                 215                 220

Arg Glu Ile Met Gly Ser Ser Ile Ser Ala Asn Cys Lys Ser Leu Ser
225                 230                 235                 240

Gly Thr Ser Val Ala Ser Pro Val Val Ala Gly Val Val Cys Leu Leu
                245                 250                 255

Val Ser Val Ile Pro Glu His Asp Arg Lys Asn Ile Leu Asn Pro Ala
                260                 265                 270

Ser Met Lys Gln Ala Leu Val Glu Gly Ala Ala Arg Leu Pro Asp Ala
            275                 280                 285

Asn Met Tyr Glu Gln Gly Ala Gly Arg Gly Ser Thr Ala Pro Pro Ala
        290                 295                 300

Arg Val Cys Glu Ser Gln Ser His Lys Phe Glu Gly Ala Cys Met Gly
305                 310                 315                 320

Asp His Asn Cys Ala Leu Val Cys Arg Asn Glu Gly Phe Ser Gly Gly
                325                 330                 335

Lys Cys Lys Gly Leu Arg Arg Arg Cys Phe Cys Thr Lys Leu Cys Val
                340                 345                 350

Phe Asp Glu Lys
        355

<210> SEQ ID NO 8
<211> LENGTH: 380
<212> TYPE: PRT
<213> ORGANISM: Artificial Sequence
<220> FEATURE:
<223> OTHER INFORMATION: synthetic contruct

<400> SEQUENCE: 8

Met Ile Tyr Ala Phe Arg Ile Thr Leu Ile Tyr Thr Tyr Ser Asn Ser
 1               5                  10                  15

Ile Asn Gly Phe Ser Ala Ser Leu Thr Leu Ser Glu Leu Glu Ala Leu
                20                  25                  30

Lys Lys Ser Pro Gly Tyr Leu Ser Ser Thr Pro Asp Gln Phe Val Gln
            35                  40                  45
```

Pro His Thr Thr Arg Ser His Glu Phe Leu Gly Leu Arg Arg Gly Ser
    50                  55                  60

Gly Ala Trp Thr Ala Ser Asn Tyr Gly Asn Gly Val Ile Ile Gly Leu
 65                  70                  75                  80

Val Asp Ser Gly Ile Trp Pro Glu Ser Ala Ser Phe Lys Asp Glu Gly
                 85                  90                  95

Met Gly Lys Pro Pro Arg Trp Lys Gly Ala Cys Val Ala Asp Ala
            100                 105                 110

Asn Phe Thr Ser Ser Met Cys Asn Asn Lys Ile Ile Gly Ala Arg Tyr
            115                 120                 125

Tyr Asn Arg Gly Phe Leu Ala Lys Tyr Pro Asp Glu Thr Ile Ser Met
130                 135                 140

Asn Ser Ser Arg Asp Ser Glu Gly His Gly Thr His Thr Ser Ser Thr
145                 150                 155                 160

Ala Ala Gly Ala Phe Val Glu Gly Val Ser Tyr Phe Gly Tyr Ala Asn
                165                 170                 175

Gly Thr Ala Ala Gly Met Ala Pro Arg Ala Trp Ile Ala Val Tyr Lys
                180                 185                 190

Ala Ile Trp Ser Gly Arg Ile Ala Gln Ser Asp Ala Leu Ala Ala Ile
                195                 200                 205

Asp Gln Ala Ile Glu Asp Gly Val Asp Ile Leu Ser Leu Ser Phe Ser
210                 215                 220

Phe Gly Asn Asn Ser Leu Asn Leu Asn Pro Ile Ser Ile Ala Cys Phe
225                 230                 235                 240

Thr Ala Met Glu Lys Gly Ile Phe Val Ala Ala Ser Ala Gly Asn Asp
                245                 250                 255

Gly Asn Ala Phe Gly Thr Leu Ser Asn Gly Glu Pro Trp Val Thr Thr
                260                 265                 270

Val Gly Ala Glu Met Gly Thr Lys Pro Ala Pro Met Val Asp Ile Tyr
                275                 280                 285

Ser Ser Arg Gly Pro Phe Ile Gln Cys Pro Asn Val Leu Lys Pro Asp
290                 295                 300

Ile Leu Ala Pro Gly Thr Ser Val Leu Ala Ala Trp Pro Ser Asn Thr
305                 310                 315                 320

Pro Val Ser Asp Asn Phe Tyr His Gln Trp Tyr Ser Asp Phe Asn Val
                325                 330                 335

Leu Ser Gly Thr Ser Met Ala Thr Ala His Val Ala Gly Val Ala Ala
                340                 345                 350

Leu Val Lys Ala Val His Pro Asn Trp Ser Pro Ala Ala Ile Arg Ser
355                 360                 365

Ala Leu Met Thr Thr Ala Asn Thr Leu Asp Asn Thr
370                 375                 380

<210> SEQ ID NO 9
<211> LENGTH: 77
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthetic construct

<400> SEQUENCE: 9

Met Lys Gly Ser Gln Arg Leu Phe Ser Ala Phe Leu Leu Val Ile Leu
 1               5                  10                  15

```
Leu Phe Met Ala Thr Glu Met Gly Pro Met Val Ala Glu Ala Arg Thr
            20                  25                  30
Cys Glu Ser Gln Ser His Arg Phe Lys Gly Thr Cys Val Arg Gln Ser
        35                  40                  45
Asn Cys Ala Ala Val Cys Gln Thr Glu Gly Phe His Gly Gly Asn Cys
    50                  55                  60
Arg Gly Phe Arg Arg Arg Cys Phe Cys Thr Lys His Cys
65                  70                  75

<210> SEQ ID NO 10
<211> LENGTH: 93
<212> TYPE: PRT
<213> ORGANISM: Artificial Sequence
<220> FEATURE:
<223> OTHER INFORMATION: synthetic construct

<400> SEQUENCE: 10

Met Lys His Leu Glu Asp Leu Lys Phe Lys Lys Lys Met Thr Lys
1               5                   10                  15
Lys Lys Glu Glu Ala Met Glu Lys Lys Ser Pro Leu Gly Leu Thr Phe
            20                  25                  30
Leu Leu Leu Leu Leu Leu Met Ala Ser Gln Glu Thr Glu Ala Arg Leu
        35                  40                  45
Cys Glu Ser Gln Ser His Trp Phe Arg Gly Val Cys Val Ser Asn His
    50                  55                  60
Asn Cys Ala Val Val Cys Arg Asn Glu His Phe Val Gly Gly Arg Cys
65                  70                  75                  80
Arg Gly Phe Arg Arg Arg Cys Phe Cys Thr Arg Asn Cys
                85                  90

<210> SEQ ID NO 11
<211> LENGTH: 285
<212> TYPE: PRT
<213> ORGANISM: Artificial Sequence
<220> FEATURE:
<223> OTHER INFORMATION: synthetic construct

<400> SEQUENCE: 11

Met Gly Leu Ser Ser Asn Leu Met Ala Pro Ala Ala Phe Phe Ile Val
1               5                   10                  15
Leu Ala Leu Phe Ser Val Pro Thr Asp Ala Gln Ile Lys Ser Asp Glu
            20                  25                  30
Gly Phe Ile Ser Val Phe Ile Ser Ser Lys Gly Leu Gly Phe Val Lys
        35                  40                  45
Asp Leu Leu Met His Lys Ala Val Ser Ser Leu Thr Pro Ile Glu Ile
    50                  55                  60
Gln Pro Ile Glu Lys Ile Val Lys Ile Pro Leu Val Gly Gln Val Asp
65                  70                  75                  80
Ile Leu Leu Ser Asn Ile Thr Ile Leu Ser Val Gly Val Gly Thr Ser
                85                  90                  95
Tyr Val Ser Ser Gly Ala Gly Val Val Ile Val Ala Ser Gly Gly
            100                 105                 110
Thr Ala Asn Met Ser Met Asn Trp Lys Tyr Ser Tyr Asp Thr Trp Leu
        115                 120                 125
Phe Pro Ile Ser Asp Lys Gly Ala Ala Ser Val Leu Val Glu Gly Met
    130                 135                 140
Ala Met Glu Leu Thr Leu Gly Leu Lys Asp Gln Asn Gly Thr Leu Ser
```

```
145                 150                 155                 160
Leu Ser Leu Leu Asp Trp Gly Cys Phe Val Lys Asp Ile Phe Val Lys
                165                 170                 175

Leu Asp Gly Gly Ala Thr Trp Phe Tyr Gln Gly Leu Val Asp Ala Phe
            180                 185                 190

Lys Glu Gln Ile Ala Ser Ala Val Glu Asp Ser Val Ser Lys Arg Ile
        195                 200                 205

Arg Glu Gly Ile Ile Lys Leu Asp Ser Leu Leu Gln Ser Val Pro Lys
    210                 215                 220

Glu Ile Pro Val Asp His Val Ala Ala Leu Asn Val Thr Phe Val Lys
225                 230                 235                 240

Asp Pro Val Ser Ser Asn Ser Ser Ile Asp Phe Glu Ile Asn Gly Leu
                245                 250                 255

Phe Thr Ala Lys Asp Gly Ile Pro Ala Pro Thr Asn Tyr His Lys Lys
            260                 265                 270

His Arg Ala Pro Val Ser Cys Thr Gly Pro Ala Lys Met
        275                 280                 285

<210> SEQ ID NO 12
<211> LENGTH: 240
<212> TYPE: PRT
<213> ORGANISM: Artificial Sequence
<220> FEATURE:
<223> OTHER INFORMATION: synthetic construct

<400> SEQUENCE: 12

Met Gly Leu Ser Ser Asn Leu Met Ala Pro Ala Phe Phe Ile Val
1               5                   10                  15

Leu Ala Leu Phe Ser Val Pro Thr Asp Ala Gln Ile Lys Ser Asp Glu
                20                  25                  30

Gly Phe Ile Ser Val Phe Ile Ser Ser Lys Gly Leu Gly Phe Val Lys
            35                  40                  45

Asp Leu Leu Met His Lys Ala Val Ser Ser Leu Thr Pro Ile Glu Ile
        50                  55                  60

Gln Pro Ile Glu Lys Ile Val Lys Ile Pro Leu Val Gly Gln Val Asp
65                  70                  75                  80

Ile Leu Leu Ser Asn Ile Thr Ile Leu Ser Val Gly Val Gly Thr Ser
                85                  90                  95

Tyr Val Ser Ser Gly Ala Gly Val Val Ile Val Ala Ser Gly Gly
            100                 105                 110

Thr Ala Asn Met Ser Met Asn Trp Lys Tyr Ser Tyr Asp Thr Trp Leu
        115                 120                 125

Phe Pro Ile Ser Asp Lys Gly Ala Ala Ser Val Leu Val Glu Gly Met
    130                 135                 140

Ala Met Glu Leu Thr Leu Gly Leu Lys Asp Gln Asn Gly Thr Leu Ser
145                 150                 155                 160

Leu Ser Leu Leu Asp Trp Gly Cys Phe Val Lys Asp Ile Phe Val Lys
                165                 170                 175

Leu Asp Gly Gly Ala Thr Trp Phe Tyr Gln Gly Leu Val Asp Ala Phe
            180                 185                 190

Lys Glu Gln Ile Ala Ser Ala Val Glu Asp Ser Val Ser Lys Arg Ile
        195                 200                 205

Arg Glu Gly Ile Ile Lys Leu Asp Ser Leu Leu Gln Ser Val Pro Lys
    210                 215                 220

Glu Ile Pro Val Asp His Val Ala Ala Leu Asn Val Thr Phe Val Lys
```

<210> SEQ ID NO 13
<211> LENGTH: 40
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthetic construct

<400> SEQUENCE: 13

```
Met Val Ala Ser Arg Ser Ser Phe Ala Tyr Tyr Phe Leu Leu Val Leu
1               5                  10                  15

Val Ser Phe Cys Leu Leu Arg Leu Gly Asp Arg Ile Asn Tyr Glu Thr
            20                  25                  30

Leu Thr Leu Thr Pro Pro Arg Thr
            35                  40
```

<210> SEQ ID NO 14
<211> LENGTH: 267
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthetic construct

<400> SEQUENCE: 14

```
Gly Leu Trp Glu Lys Gly Tyr Thr Gly Ala Lys Val Lys Met Ala Ile
1               5                  10                  15

Phe Asp Thr Gly Ile Arg Ala Asn His Pro His Phe Arg Asn Ile Lys
            20                  25                  30

Glu Arg Thr Asn Trp Thr Asn Glu Asp Thr Leu Asn Asp Asn Leu Gly
        35                  40                  45

His Gly Thr Phe Val Ala Gly Val Ile Ala Gly Gln Tyr Asp Glu Cys
    50                  55                  60

Leu Gly Phe Ala Pro Asp Thr Glu Ile Tyr Ala Phe Arg Val Phe Thr
65                  70                  75                  80

Asp Ala Gln Val Ser Tyr Thr Ser Trp Phe Leu Asp Ala Phe Asn Tyr
                85                  90                  95

Ala Ile Ala Thr Asn Met Asp Val Leu Asn Leu Ser Ile Gly Gly Pro
            100                 105                 110

Asp Tyr Leu Asp Leu Pro Phe Val Glu Lys Val Trp Glu Leu Thr Ala
        115                 120                 125

Asn Asn Ile Ile Met Val Ser Ala Ile Gly Asn Asp Gly Pro Leu Tyr
    130                 135                 140

Gly Thr Leu Asn Asn Pro Ala Asp Gln Ser Asp Val Ile Gly Val Ile
145                 150                 155                 160

Asp Tyr Gly Asp His Ile Ala Ser Phe Ser Ser Arg Gly Met Ser Thr
                165                 170                 175

Trp Glu Ile Pro His Gly Tyr Gly Arg Val Lys Pro Asp Val Val Ala
            180                 185                 190

Tyr Gly Arg Glu Ile Met Gly Ser Ser Ile Ser Ala Asn Cys Lys Ser
        195                 200                 205

Leu Ser Gly Thr Ser Val Ala Ser Pro Val Val Ala Gly Val Val Cys
    210                 215                 220
```

```
Leu Leu Val Ser Val Ile Pro Glu His Asp Arg Lys Asn Ile Leu Asn
225                 230                 235                 240

Pro Ala Ser Met Lys Gln Ala Leu Val Glu Gly Ala Ala Arg Leu Pro
                245                 250                 255

Asp Ala Asn Met Tyr Glu Gln Gly Ala Gly Arg
                260                 265

<210> SEQ ID NO 15
<211> LENGTH: 52
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthetic construct

<400> SEQUENCE: 15

Arg Val Cys Glu Ser Gln Ser His Lys Phe Glu Gly Ala Cys Met Gly
1               5                   10                  15

Asp His Asn Cys Ala Leu Val Cys Arg Asn Glu Gly Phe Ser Gly Gly
                20                  25                  30

Lys Cys Lys Gly Leu Arg Arg Arg Cys Phe Cys Thr Lys Leu Cys Val
            35                  40                  45

Phe Asp Glu Lys
    50

<210> SEQ ID NO 16
<211> LENGTH: 221
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthetic construct

<400> SEQUENCE: 16

Ser Ser Gln Gly Leu Asp Phe Ile Lys Asn Leu Leu Ile Thr Lys Ala
1               5                   10                  15

Ile Ser Ser Leu Thr Pro Leu Gln Leu Pro Gln Ile Lys Lys Ser Val
                20                  25                  30

Lys Ile Pro Phe Leu Gly Arg Val Asp Ile Ala Phe Ser Asn Ile Thr
            35                  40                  45

Ile Tyr His Ile Asp Val Ser Ser Ser Asn Ile Ala Pro Gly Asp Thr
        50                  55                  60

Gly Val Ala Ile Ile Ala Ser Gly Thr Thr Cys Asn Leu Ser Met Asn
65                  70                  75                  80

Trp His Tyr Ser Tyr Asn Thr Trp Phe Val Pro Val Glu Ile Ser Asp
                85                  90                  95

Ser Gly Thr Ala Gln Val Gln Val Glu Gly Met Glu Val Gly Leu Thr
                100                 105                 110

Leu Gly Leu Glu Asn Arg Glu Gly Ser Met Lys Leu Ser Ala Lys Asp
            115                 120                 125

Cys Gly Cys Tyr Val Glu Asp Ile Ser Ile Lys Leu Asp Gly Gly Ala
        130                 135                 140

Ser Trp Leu Tyr Gln Gly Val Val Asp Ala Phe Glu Glu Gln Ile Gly
145                 150                 155                 160

Ser Ala Val Glu Ser Thr Ile Thr Lys Lys Leu Lys Glu Gly Ile Ile
                165                 170                 175
```

Lys Leu Asp Ser Phe Leu Gln Ala Leu Pro Lys Glu Ile Pro Val Asp
            180                 185                 190

Asn Ile Ala Ser Leu Asn Val Thr Phe Val Asn Asp Pro Leu Leu Ser
        195                 200                 205

Asn Ser Ser Ile Gly Phe Asp Ile Asn Gly Leu Phe Thr
    210                 215                 220

<210> SEQ ID NO 17
<211> LENGTH: 27
<212> TYPE: PRT
<213> ORGANISM: Artificial Sequence
<220> FEATURE:
<223> OTHER INFORMATION: synthetic construct

<400> SEQUENCE: 17

Ala Lys Asp Gly Ile Pro Ala Pro Thr Asn Tyr His Lys Lys His Arg
1               5                   10                  15

Ala Pro Val Ser Cys Thr Gly Pro Ala Lys Met
            20                  25

<210> SEQ ID NO 18
<211> LENGTH: 7
<212> TYPE: PRT
<213> ORGANISM: Artificial Sequence
<220> FEATURE:
<223> OTHER INFORMATION: synthetic construct

<400> SEQUENCE: 18

Gly Ser Thr Ala Pro Pro Ala
1               5

<210> SEQ ID NO 19
<211> LENGTH: 25
<212> TYPE: PRT
<213> ORGANISM: Artificial Sequence
<220> FEATURE:
<223> OTHER INFORMATION: synthetic construct

<400> SEQUENCE: 19

Arg Ala Asn Ala Thr Thr Leu Pro Lys Tyr Tyr Gln Asn Ser Arg His
1               5                   10                  15

Pro Val Ser Cys Thr Asp Pro Ser Lys
            20                  25

<210> SEQ ID NO 20
<211> LENGTH: 14
<212> TYPE: PRT
<213> ORGANISM: Artificial Sequence
<220> FEATURE:
<223> OTHER INFORMATION: synthetic construct

<400> SEQUENCE: 20

Gly Ser Thr Ala Pro Pro Ala Gly Ser Thr Ala Pro Pro Ala
1               5                   10

<210> SEQ ID NO 21
<211> LENGTH: 15
<212> TYPE: PRT
<213> ORGANISM: Artificial Sequence
<220> FEATURE:
<223> OTHER INFORMATION: synthetic construct

<400> SEQUENCE: 21

Gln Ala Ser His Thr Cys Val Cys Glu Phe Asn Cys Ala Pro Leu

-continued

```
1               5                   10                  15

<210> SEQ ID NO 22
<211> LENGTH: 27
<212> TYPE: PRT
<213> ORGANISM: Artificial Sequence
<220> FEATURE:
<223> OTHER INFORMATION: synthetic construct

<400> SEQUENCE: 22

Ala Arg Lys Lys Ala Ser Ile Pro Asn Tyr Tyr Asn Ser Asn Leu Gln
1               5                   10                  15

Pro Pro Val Phe Cys Ser Asp Gln Ser Lys Met
            20                  25

<210> SEQ ID NO 23
<211> LENGTH: 14
<212> TYPE: PRT
<213> ORGANISM: Artificial Sequence
<220> FEATURE:
<223> OTHER INFORMATION: synthetic construct

<400> SEQUENCE: 23

Tyr Glu Gln Gly Ala Gly Arg Gly Ser Thr Ala Pro Pro Ala
1               5                   10

<210> SEQ ID NO 24
<211> LENGTH: 40
<212> TYPE: PRT
<213> ORGANISM: Artificial Sequence
<220> FEATURE:
<223> OTHER INFORMATION: synthetic construct

<400> SEQUENCE: 24

Met Val Ala Ser Arg Ser Ser Phe Ala Tyr Tyr Phe Leu Leu Val Leu
1               5                   10                  15

Val Ser Phe Cys Leu Leu Arg Leu Gly Asp Arg Ile Asn Tyr Glu Thr
            20                  25                  30

Leu Thr Leu Thr Pro Pro Arg Thr
        35                  40

<210> SEQ ID NO 25
<211> LENGTH: 25
<212> TYPE: PRT
<213> ORGANISM: Artificial Sequence
<220> FEATURE:
<223> OTHER INFORMATION: synthetic construct

<400> SEQUENCE: 25

Met Gly Lys His His Val Thr Leu Cys Cys Val Val Phe Ala Val Leu
1               5                   10                  15

Cys Leu Ala Ser Ser Leu Ala Gln Ala
            20                  25

<210> SEQ ID NO 26
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthesized

<400> SEQUENCE: 26
```

```
Met Glu Leu Lys Phe Ser Thr Phe Leu Ser Leu Thr Leu Leu Phe Ser
1               5                   10                  15

Ser Val Leu Asn Pro Ala Leu Ser
            20
```

<210> SEQ ID NO 27
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<223> OTHER INFORMATION: synthesized construct

<400> SEQUENCE: 27

```
Gly Ser Thr Ala
1
```

<210> SEQ ID NO 28
<211> LENGTH: 11
<212> TYPE: PRT
<213> ORGANISM: Artificial Sequence
<220> FEATURE:
<223> OTHER INFORMATION: synthetic construct

<400> SEQUENCE: 28

```
Gly Gly Gly Ser Gly Gly Gly Thr Asp Gly Arg
1               5                   10
```

<210> SEQ ID NO 29
<211> LENGTH: 5
<212> TYPE: PRT
<213> ORGANISM: Artificial Sequence
<220> FEATURE:
<223> OTHER INFORMATION: synthetic construct

<400> SEQUENCE: 29

```
Val Phe Asp Glu Lys
1               5
```

<210> SEQ ID NO 30
<211> LENGTH: 297
<212> TYPE: PRT
<213> ORGANISM: Artificial Sequence
<220> FEATURE:
<223> OTHER INFORMATION: synthetic construct

<400> SEQUENCE: 30

```
Ser Gln Gly Leu Asp Phe Ile Lys Asn Leu Leu Ile Thr Lys Ala Ile
1               5                   10                  15

Ser Ser Leu Thr Pro Leu Gln Leu Pro Gln Ile Lys Lys Ser Val Lys
            20                  25                  30

Ile Pro Phe Leu Gly Arg Val Asp Ile Ala Phe Ser Asn Ile Thr Ile
            35                  40                  45

Tyr His Ile Asp Val Ser Ser Asn Ile Ala Pro Gly Asp Thr Gly
        50                  55                  60

Val Ala Ile Ile Ala Ser Gly Thr Thr Cys Asn Leu Ser Met Asn Trp
65                  70                  75                  80

His Tyr Ser Tyr Asn Thr Trp Phe Val Pro Val Glu Ile Ser Asp Ser
                85                  90                  95

Gly Thr Ala Gln Val Gln Val Glu Gly Met Glu Val Gly Leu Thr Leu
            100                 105                 110
```

Gly Leu Glu Asn Arg Glu Gly Ser Met Lys Leu Ser Ala Lys Asp Cys
            115                 120                 125

Gly Cys Tyr Val Glu Asp Ile Ser Ile Lys Leu Asp Gly Gly Ala Ser
        130                 135                 140

Trp Leu Tyr Gln Gly Val Val Asp Ala Phe Glu Glu Gln Ile Gly Ser
145                 150                 155                 160

Ala Val Glu Ser Thr Ile Thr Lys Lys Leu Lys Glu Gly Ile Ile Lys
                165                 170                 175

Leu Asp Ser Phe Leu Gln Ala Leu Pro Lys Glu Ile Pro Val Asp Asn
            180                 185                 190

Ile Ala Ser Leu Asn Val Thr Phe Val Asn Asp Pro Leu Leu Ser Asn
        195                 200                 205

Ser Ser Ile Gly Phe Asp Ile Asn Gly Leu Phe Thr Arg Ala Asn Ala
    210                 215                 220

Thr Thr Leu Pro Lys Tyr Tyr Gln Asn Ser Arg His Pro Val Ser Cys
225                 230                 235                 240

Thr Asp Pro Ser Lys Arg Val Cys Glu Ser Gln Ser His Lys Phe Glu
                245                 250                 255

Gly Ala Cys Met Gly Asp His Asn Cys Ala Leu Val Cys Arg Asn Glu
            260                 265                 270

Gly Phe Ser Gly Gly Lys Cys Lys Gly Leu Arg Arg Arg Cys Phe Cys
        275                 280                 285

Thr Lys Leu Cys Val Phe Asp Glu Lys
    290                 295

<210> SEQ ID NO 31
<211> LENGTH: 278
<212> TYPE: PRT
<213> ORGANISM: Artificial Sequence
<220> FEATURE:
<223> OTHER INFORMATION: synthetic construct

<400> SEQUENCE: 31

Arg Val Cys Glu Ser Gln Ser His Lys Phe Glu Gly Ala Cys Met Gly
1               5                   10                  15

Asp His Asn Cys Ala Leu Val Cys Arg Asn Glu Gly Phe Ser Gly Gly
            20                  25                  30

Lys Cys Lys Gly Leu Arg Arg Arg Cys Phe Cys Thr Lys Leu Cys Val
        35                  40                  45

Phe Asp Glu Lys Gly Ser Thr Ala Pro Pro Ala Ser Ser Gln Gly Leu
    50                  55                  60

Asp Phe Ile Lys Asn Leu Leu Ile Thr Lys Ala Ile Ser Ser Leu Thr
65                  70                  75                  80

Pro Leu Gln Leu Pro Gln Ile Lys Lys Ser Val Lys Ile Pro Phe Leu
                85                  90                  95

Gly Arg Val Asp Ile Ala Phe Ser Asn Ile Thr Ile Tyr His Ile Asp
            100                 105                 110

Val Ser Ser Ser Asn Ile Ala Pro Gly Asp Thr Gly Val Ala Ile Ile
        115                 120                 125

Ala Ser Gly Thr Thr Cys Asn Leu Ser Met Asn Trp His Tyr Ser Tyr
    130                 135                 140

Asn Thr Trp Phe Val Pro Val Glu Ile Ser Asp Ser Gly Thr Ala Gln
145                 150                 155                 160

Val Gln Val Glu Gly Met Glu Val Gly Leu Thr Leu Gly Leu Glu Asn
                165                 170                 175

```
Arg Glu Gly Ser Met Lys Leu Ser Ala Lys Asp Cys Gly Cys Tyr Val
                180                 185                 190

Glu Asp Ile Ser Ile Lys Leu Asp Gly Gly Ala Ser Trp Leu Tyr Gln
            195                 200                 205

Gly Val Val Asp Ala Phe Glu Glu Gln Ile Gly Ser Ala Val Glu Ser
        210                 215                 220

Thr Ile Thr Lys Lys Leu Lys Glu Gly Ile Ile Lys Leu Asp Ser Phe
225                 230                 235                 240

Leu Gln Ala Leu Pro Lys Glu Ile Pro Val Asp Asn Ile Ala Ser Leu
                245                 250                 255

Asn Val Thr Phe Val Asn Asp Pro Leu Leu Ser Asn Ser Ser Ile Gly
            260                 265                 270

Phe Asp Ile Asn Gly Leu
            275

<210> SEQ ID NO 32
<211> LENGTH: 327
<212> TYPE: PRT
<213> ORGANISM: Artificial Sequence
<220> FEATURE:
<223> OTHER INFORMATION: synthetic construct

<400> SEQUENCE: 32

Arg Val Cys Glu Ser Gln Ser His Lys Phe Glu Gly Ala Cys Met Gly
1               5                   10                  15

Asp His Asn Cys Ala Leu Val Cys Arg Asn Glu Gly Phe Ser Gly Gly
                20                  25                  30

Lys Cys Lys Gly Leu Arg Arg Arg Cys Phe Cys Thr Lys Leu Cys Val
            35                  40                  45

Phe Asp Glu Lys Gly Ser Thr Ala Pro Pro Ala Arg Gly Leu Trp Glu
        50                  55                  60

Lys Gly Tyr Thr Gly Ala Lys Val Lys Met Ala Ile Phe Asp Thr Gly
65                  70                  75                  80

Ile Arg Ala Asn His Pro His Phe Arg Asn Ile Lys Glu Arg Thr Asn
                85                  90                  95

Trp Thr Asn Glu Asp Thr Leu Asn Asp Asn Leu Gly His Gly Thr Phe
            100                 105                 110

Val Ala Gly Val Ile Ala Gly Gln Tyr Asp Glu Cys Leu Gly Phe Ala
        115                 120                 125

Pro Asp Thr Glu Ile Tyr Ala Phe Arg Val Phe Thr Asp Ala Gln Val
    130                 135                 140

Ser Tyr Thr Ser Trp Phe Leu Asp Ala Phe Asn Tyr Ala Ile Ala Thr
145                 150                 155                 160

Asn Met Asp Val Leu Asn Leu Ser Ile Gly Gly Pro Asp Tyr Leu Asp
                165                 170                 175

Leu Pro Phe Val Glu Lys Val Trp Glu Leu Thr Ala Asn Asn Ile Ile
            180                 185                 190

Met Val Ser Ala Ile Gly Asn Asp Gly Pro Leu Tyr Gly Thr Leu Asn
        195                 200                 205

Asn Pro Ala Asp Gln Ser Asp Val Ile Gly Val Ile Asp Tyr Gly Asp
    210                 215                 220

His Ile Ala Ser Phe Ser Ser Arg Gly Met Ser Thr Trp Glu Ile Pro
225                 230                 235                 240

His Gly Tyr Gly Arg Val Lys Pro Asp Val Val Ala Tyr Gly Arg Glu
                245                 250                 255
```

Ile Met Gly Ser Ser Ile Ser Ala Asn Cys Lys Ser Leu Ser Gly Thr
                260                 265                 270

Ser Val Ala Ser Pro Val Val Ala Gly Val Val Cys Leu Leu Val Ser
            275                 280                 285

Val Ile Pro Glu His Asp Arg Lys Asn Ile Leu Asn Pro Ala Ser Met
        290                 295                 300

Lys Gln Ala Leu Val Glu Gly Ala Ala Arg Leu Pro Asp Ala Asn Met
305                 310                 315                 320

Tyr Glu Gln Gly Ala Gly Arg
                325

<210> SEQ ID NO 33
<211> LENGTH: 326
<212> TYPE: PRT
<213> ORGANISM: Artificial Sequence
<220> FEATURE:
<223> OTHER INFORMATION: synthetic construct

<400> SEQUENCE: 33

Gly Leu Trp Glu Lys Gly Tyr Thr Gly Ala Lys Val Lys Met Ala Ile
1               5                   10                  15

Phe Asp Thr Gly Ile Arg Ala Asn His Pro His Phe Arg Asn Ile Lys
            20                  25                  30

Glu Arg Thr Asn Trp Thr Asn Glu Asp Thr Leu Asn Asp Asn Leu Gly
        35                  40                  45

His Gly Thr Phe Val Ala Gly Val Ile Ala Gly Gln Tyr Asp Glu Cys
    50                  55                  60

Leu Gly Phe Ala Pro Asp Thr Glu Ile Tyr Ala Phe Arg Val Phe Thr
65                  70                  75                  80

Asp Ala Gln Val Ser Tyr Thr Ser Trp Phe Leu Asp Ala Phe Asn Tyr
                85                  90                  95

Ala Ile Ala Thr Asn Met Asp Val Leu Asn Leu Ser Ile Gly Gly Pro
            100                 105                 110

Asp Tyr Leu Asp Leu Pro Phe Val Glu Lys Val Trp Glu Leu Thr Ala
        115                 120                 125

Asn Asn Ile Ile Met Val Ser Ala Ile Gly Asn Asp Gly Pro Leu Tyr
    130                 135                 140

Gly Thr Leu Asn Asn Pro Ala Asp Gln Ser Asp Val Ile Gly Val Ile
145                 150                 155                 160

Asp Tyr Gly Asp His Ile Ala Ser Phe Ser Ser Arg Gly Met Ser Thr
                165                 170                 175

Trp Glu Ile Pro His Gly Tyr Gly Arg Val Lys Pro Asp Val Val Ala
            180                 185                 190

Tyr Gly Arg Glu Ile Met Gly Ser Ser Ile Ser Ala Asn Cys Lys Ser
        195                 200                 205

Leu Ser Gly Thr Ser Val Ala Ser Pro Val Val Ala Gly Val Val Cys
    210                 215                 220

Leu Leu Val Ser Val Ile Pro Glu His Asp Arg Lys Asn Ile Leu Asn
225                 230                 235                 240

Pro Ala Ser Met Lys Gln Ala Leu Val Glu Gly Ala Ala Arg Leu Pro
                245                 250                 255

Asp Ala Asn Met Tyr Glu Gln Gly Ala Gly Arg Gly Ser Thr Ala Pro
            260                 265                 270

Pro Ala Arg Val Cys Gly Ser Gln Ser His Lys Phe Glu Gly Ala Cys
        275                 280                 285

```
Met Gly Asp His Asn Cys Ala Leu Val Cys Arg Asn Glu Gly Phe Ser
            290                 295                 300
Gly Gly Lys Cys Lys Gly Leu Arg Arg Arg Cys Phe Cys Thr Lys Leu
305                 310                 315                 320
Cys Val Phe Asp Glu Lys
                325
```

<210> SEQ ID NO 34
<211> LENGTH: 255
<212> TYPE: PRT
<213> ORGANISM: Artificial Sequence
<220> FEATURE:
<223> OTHER INFORMATION: synthetic construct

<400> SEQUENCE: 34

```
Met Arg Pro Ser Val Leu Val Ile Phe Ile Ala Phe Leu Leu Phe Thr
1               5                   10                  15
Pro Ser Gln Ala His Leu Lys Ser Thr Glu Ser Ser Phe Ile Ser Ile
            20                  25                  30
Leu Ile Ser Ser Gln Gly Leu Asp Phe Ile Lys Asn Leu Leu Ile Thr
        35                  40                  45
Lys Ala Ile Ser Ser Leu Thr Pro Leu Gln Leu Pro Gln Ile Lys Lys
50                  55                  60
Ser Val Lys Ile Pro Phe Leu Gly Arg Val Asp Ile Ala Phe Ser Asn
65                  70                  75                  80
Ile Thr Ile Tyr His Ile Asp Val Ser Ser Asn Ile Ala Pro Gly
                85                  90                  95
Asp Thr Gly Val Ala Ile Ile Ala Ser Gly Thr Thr Cys Asn Leu Ser
                100                 105                 110
Met Asn Trp His Tyr Ser Tyr Asn Thr Trp Phe Val Pro Val Glu Ile
            115                 120                 125
Ser Asp Ser Gly Thr Ala Gln Val Gln Val Glu Gly Met Glu Val Gly
130                 135                 140
Leu Thr Leu Gly Leu Glu Asn Arg Glu Gly Ser Met Lys Leu Ser Ala
145                 150                 155                 160
Lys Asp Cys Gly Cys Tyr Val Glu Asp Ile Ser Ile Lys Leu Asp Gly
                165                 170                 175
Gly Ala Ser Trp Leu Tyr Gln Gly Val Val Asp Ala Phe Glu Glu Gln
            180                 185                 190
Ile Gly Ser Ala Val Glu Ser Thr Ile Thr Lys Lys Leu Lys Glu Gly
        195                 200                 205
Ile Ile Lys Leu Asp Ser Phe Leu Gln Ala Leu Pro Lys Glu Ile Pro
    210                 215                 220
Val Asp Asn Ile Ala Ser Leu Asn Val Thr Phe Val Asn Asp Pro Leu
225                 230                 235                 240
Leu Ser Asn Ser Ser Ile Gly Phe Asp Ile Asn Gly Leu Phe Thr
                245                 250                 255
```

<210> SEQ ID NO 35
<211> LENGTH: 79
<212> TYPE: PRT
<213> ORGANISM: Artificial Sequence
<220> FEATURE:
<223> OTHER INFORMATION: synthetic construct

<400> SEQUENCE: 35

```
Met Glu Arg Lys Ser Leu Gly Phe Phe Phe Phe Leu Leu Leu Ile Leu
1               5                   10                  15
```

Leu Ala Ser Gln Met Val Val Pro Ser Glu Ala Arg Val Cys Glu Ser
        20                  25                  30

Gln Ser His Lys Phe Glu Gly Ala Cys Met Gly Asp His Asn Cys Ala
        35                  40                  45

Leu Val Cys Arg Asn Glu Gly Phe Ser Gly Gly Lys Cys Lys Gly Leu
50                  55                  60

Arg Arg Arg Cys Phe Cys Thr Lys Leu Cys Val Phe Asp Glu Lys
65                  70                  75

<210> SEQ ID NO 36
<211> LENGTH: 297
<212> TYPE: PRT
<213> ORGANISM: Artificial Sequence
<220> FEATURE:
<223> OTHER INFORMATION: synthetic construct

<400> SEQUENCE: 36

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Arg Gly Leu
                20                  25                  30

Trp Glu Lys Gly Tyr Thr Gly Ala Lys Val Lys Met Ala Ile Phe Asp
            35                  40                  45

Thr Gly Ile Arg Ala Asn His Pro His Phe Arg Asn Ile Lys Glu Arg
        50                  55                  60

Thr Asn Trp Thr Asn Glu Asp Thr Leu Asn Asp Asn Leu Gly His Gly
65                  70                  75                  80

Thr Phe Val Ala Gly Val Ile Ala Gly Gln Tyr Asp Glu Cys Leu Gly
                85                  90                  95

Phe Ala Pro Asp Thr Glu Ile Tyr Ala Phe Arg Val Phe Thr Asp Ala
            100                 105                 110

Gln Val Ser Tyr Thr Ser Trp Phe Leu Asp Ala Phe Asn Tyr Ala Ile
        115                 120                 125

Ala Thr Asn Met Asp Val Leu Asn Leu Ser Ile Gly Gly Pro Asp Tyr
130                 135                 140

Leu Asp Leu Pro Phe Val Glu Lys Val Trp Glu Leu Thr Ala Asn Asn
145                 150                 155                 160

Ile Ile Met Val Ser Ala Ile Gly Asn Asp Gly Pro Leu Tyr Gly Thr
                165                 170                 175

Leu Asn Asn Pro Ala Asp Gln Ser Asp Val Ile Gly Val Ile Asp Tyr
            180                 185                 190

Gly Asp His Ile Ala Ser Phe Ser Ser Arg Gly Met Ser Thr Trp Glu
        195                 200                 205

Ile Pro His Gly Tyr Gly Arg Val Lys Pro Asp Val Val Ala Tyr Gly
210                 215                 220

Arg Glu Ile Met Gly Ser Ser Ile Ser Ala Asn Cys Lys Ser Leu Ser
225                 230                 235                 240

Gly Thr Ser Val Ala Ser Pro Val Val Ala Gly Val Val Cys Leu Leu
                245                 250                 255

Val Ser Val Ile Pro Glu His Asp Arg Lys Asn Ile Leu Asn Pro Ala
            260                 265                 270

```
Ser Met Lys Gln Ala Leu Val Glu Gly Ala Ala Arg Leu Pro Asp Ala
        275                 280                 285

Asn Met Tyr Glu Gln Gly Ala Gly Arg
        290                 295
```